(12) United States Patent
Yamazaki et al.

(10) Patent No.: US 10,159,642 B2
(45) Date of Patent: Dec. 25, 2018

(54) FUNCTIONAL POLYMER GEL CONTAINING ORGANIC NANOTUBES AND METHOD FOR PRODUCING SAME

(71) Applicants: SEED CO., LTD., Tokyo (JP); NATIONAL INSTITUTE OF ADVANCED INDUSTRIAL SCIENCE AND TECHNOLOGY, Tokyo (JP)

(72) Inventors: Yoshiko Yamazaki, Tokyo (JP); Takao Sato, Tokyo (JP); Wuxiao Ding, Tsukuba (JP); Mitsutoshi Masuda, Tsukuba (JP); Momoyo Wada, Tsukuba (JP)

(73) Assignees: SEED CO., LTD., Tokyo (JP); NATIONAL INSTITUTE OF ADVANCED INDUSTRIAL SCIENCE AND TECHNOLOGY, Tokyo (JP)

(*) Notice: Subject to any disclaimer, the term of this patent is extended or adjusted under 35 U.S.C. 154(b) by 231 days.

(21) Appl. No.: 15/317,885

(22) PCT Filed: Jun. 12, 2015

(86) PCT No.: PCT/JP2015/067050
§ 371 (c)(1),
(2) Date: Dec. 9, 2016

(87) PCT Pub. No.: WO2015/190604
PCT Pub. Date: Dec. 17, 2015

(65) Prior Publication Data
US 2017/0112761 A1    Apr. 27, 2017

(30) Foreign Application Priority Data

Jun. 12, 2014 (JP) ................................. 2014-121914

(51) Int. Cl.
| | | |
|---|---|---|
| *A61K 9/00* | (2006.01) | |
| *A61L 27/00* | (2006.01) | |
| *A61K 9/06* | (2006.01) | |
| *A61K 47/30* | (2006.01) | |
| *A61K 47/36* | (2006.01) | |
| *A61K 47/42* | (2017.01) | |
| *C08F 6/00* | (2006.01) | |
| *A61K 31/352* | (2006.01) | |
| *A61K 31/5415* | (2006.01) | |
| *A61K 47/32* | (2006.01) | |
| *G02B 1/04* | (2006.01) | |
| *A61K 9/50* | (2006.01) | |

(52) U.S. Cl.
CPC .......... *A61K 9/0051* (2013.01); *A61K 9/0092* (2013.01); *A61K 9/06* (2013.01); *A61K 31/352* (2013.01); *A61K 31/5415* (2013.01); *A61K 47/30* (2013.01); *A61K 47/32* (2013.01); *A61K 47/36* (2013.01); *A61K 47/42* (2013.01); *A61L 27/00* (2013.01); *C08F 6/00* (2013.01); *G02B 1/043* (2013.01); *A61K 9/5057* (2013.01)

(58) Field of Classification Search
None
See application file for complete search history.

(56) References Cited

U.S. PATENT DOCUMENTS

| | | | |
|---|---|---|---|
| 6,897,326 B2 | 5/2005 | Masuda et al. | |
| 7,060,241 B2 | 6/2006 | Glatkowski | |
| 8,083,348 B2 | 12/2011 | Linhardt et al. | |
| 9,018,156 B2 | 4/2015 | Kameta et al. | |
| 2004/0076681 A1* | 4/2004 | Dennis ................ | A61K 9/0092 424/489 |
| 2006/0160248 A1 | 7/2006 | Kamiya et al. | |
| 2014/0147476 A1 | 5/2014 | Kameta et al. | |

FOREIGN PATENT DOCUMENTS

| | | |
|---|---|---|
| JP | 2002-322190 A | 11/2002 |
| JP | 2004-224717 A | 8/2004 |
| JP | 2004-526838 A | 9/2004 |
| JP | 2012-51828 A | 3/2012 |
| JP | 2012-530282 A | 11/2012 |
| WO | WO 2012/153576 A1 | 11/2012 |

OTHER PUBLICATIONS

Ding et al., "Hybrid Organic Nanotubes with Dual Functionalities Localized on Cylindrical Nanochannels Control the Release of Doxorubicin", Advanced Healthcare Materials, 2012, vol. 1, pp. 699-706. (Supporting Information is enclosed, 12 pages).
Henricus et al., "Investigation of Insulin Loaded Self-Assembled Microtubules for Drug Release", Bioconjugate Chemistry, 2008, vol. 19, No. 12, pp. 2394-2400.
International Search Report for PCT/JP2015/067050 dated Sep. 15, 2015.
Kameta et al., "Confinement Effect of Organic Nanotubes Toward Green Fluorescent Protein (GFP) Depending on the Inner Diameter Size", Chemistry A European Journal, 2010, vol. 16, pp. 4217-4223. (Supporting Information is enclosed, 4 pages).
Kameta et al., "Soft Nanotube Hydrogels Functioning as Artificial Chaperones", ACS Nano, 2012, vol. 6, No. 6, pp. 5249-5258. (Supporting Information is enclosed, 7 pages).

(Continued)

*Primary Examiner* — Susan T Tran
(74) *Attorney, Agent, or Firm* — Birch, Stewart, Kolasch & Birch, LLP

(57) ABSTRACT

The purpose of the present invention is to provide: a functional polymer gel which is able to be practically used as an ocular lens having excellent transparency and mechanical strength by uniformly dispersing organic nanotubes in a polymer gel without the formation of agglomerates of the organic nanotubes in the case where the organic nanotubes are complexed into the polymer gel; and a method for producing this functional polymer gel. The above-mentioned purpose is achieved by: a functional polymer gel which is characterized by containing organic nanotubes and having a light transmittance of 80% or more; and a method for producing this functional polymer gel.

5 Claims, 10 Drawing Sheets

(56) References Cited

OTHER PUBLICATIONS

Kameta et al., "Biologically responsive, sustainable release from metallo-drug coordinated 1D nanostructurest", Journal of Materials Chemistry B, 2013, vol. 1, pp. 276-283.

Kameta et al., "Control of Self-assembled Morphology and Molecular Packing of Asymmetric Glycolipids by Association/Dissociation with Poly(thiopheneboronic acid)", Langmuir, 2013, vol. 29, pp. 13291-13298.

Kameta et al., "Supramolecular organic nanotubes: how to utilize the inner nanospace and the outer space", Soft Matter, 2011, vol. 7, pp. 4539-4561.

Kenkyu Seika Tenkai Jigyo Kenkyu Seika Saiteki Tenkai Shien Program FS Stage Seeds Kenzaika Type Jigo Hyoka Hokokusho Yuki Nanotube o Mochiita Yakubutsu Hoshutsu Contact Lens no Kaihatsu, May 2013, 1 page.

Kogiso et al., "Instant Preparation of Self-Assembled Metal-Complexed Lipid Nanotubes That Act as Templates to Produce Metal Oxide Nanotubes", Advanced Materials, 2007, vol. 19, pp. 242-246.

Meilander et al., "Lipid-based microtubular drug delivery vehicles", Journal of Controlled Release, 2001, vol. 71, pp. 141-152.

Meilander et al., "Sustained release of plasmid DNA using lipid microtubules and agarose hydrogel", Journal of Controlled Release, 2003, vol. 88, pp. 321-331.

Written Opinion of the International Searching Authority for PCT/JP2015/067050 (PCT/ISA/237) dated Sep. 15, 2015.

Yan et al., "Transition of Cationic Dipeptide Nanotubes into Vesicles and Oligonucleotide Delivery", Angewandte Chemie, 2007, vol. 46, pp. 2431-2434. (Supporting Information is enclosed, 11 pages).

Yui et al., "Encapsulation of Ferritin within a Hollow Cylinder of Glycolipid Nanotubes", Chemistry Letters, 2005, vol. 34, No. 2, pp. 232-233.

Cirillo et al., "Carbon Nanotubes Hybrid Hydrogels in Drug Delivery: A Perspective Review," BioMed Research International (Jan. 21, 2014), vol. 2014, Article ID 825017, pp. 1-17.

Extended European Search Report dated Dec. 7, 2017, in European Patent Application No. 15805888.3.

* cited by examiner

[FIG.1]
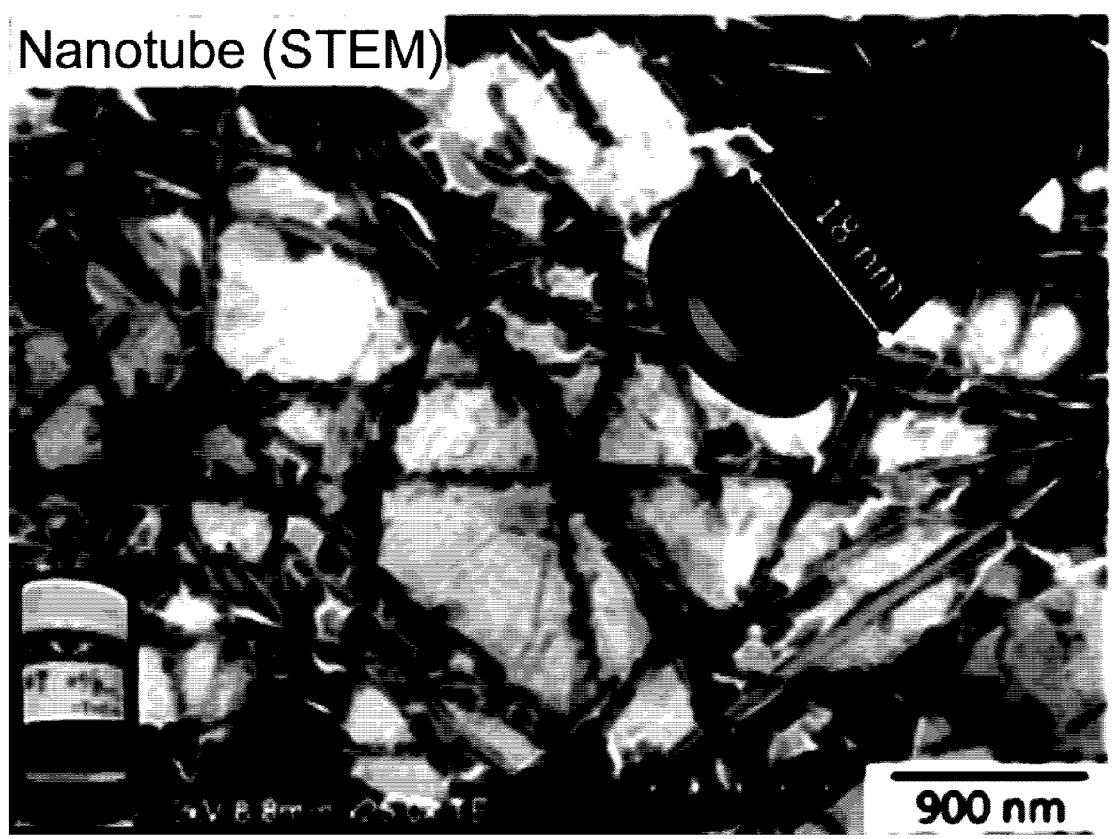

[FIG.2]
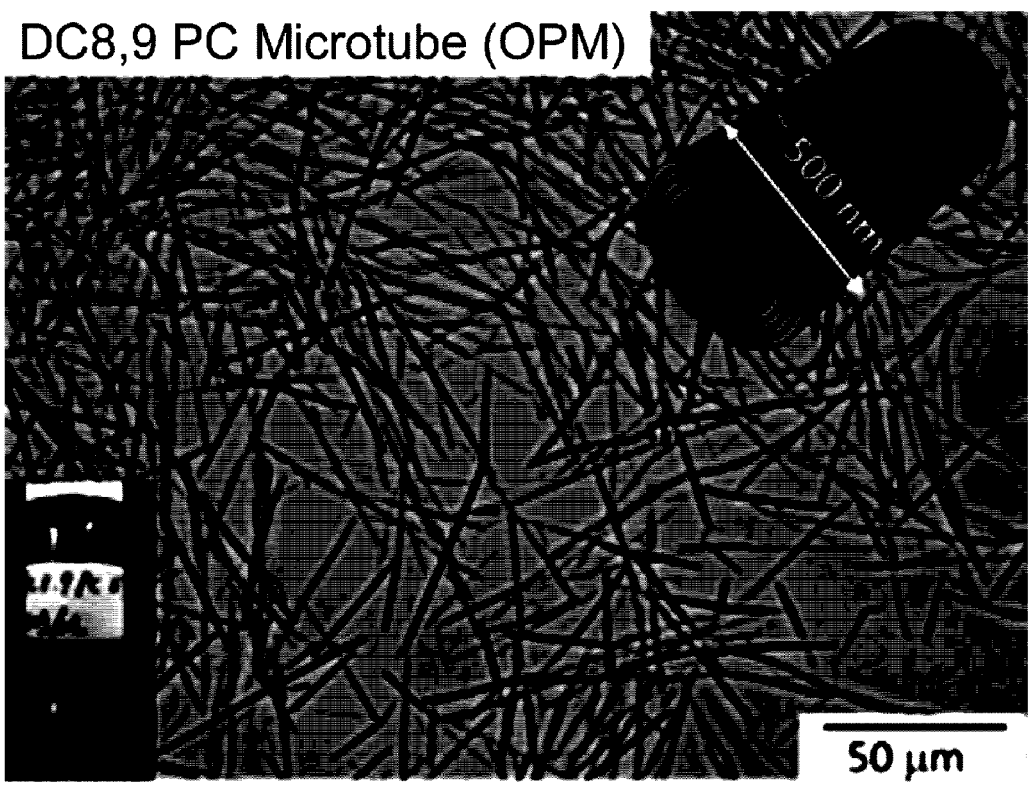

[FIG.3]
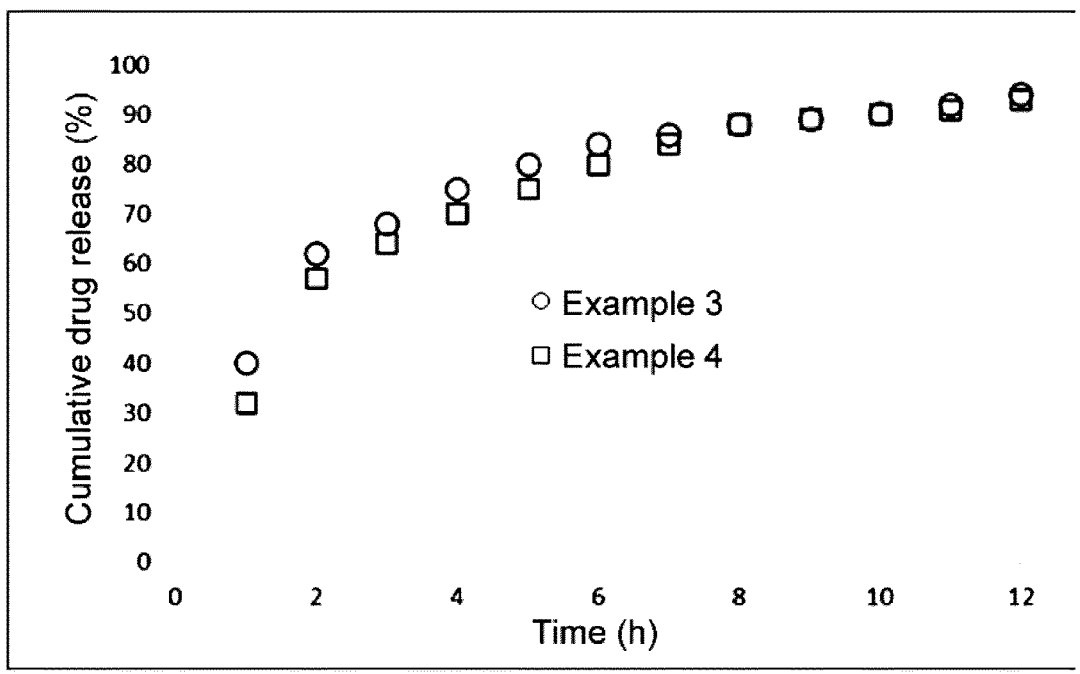

[FIG.4]
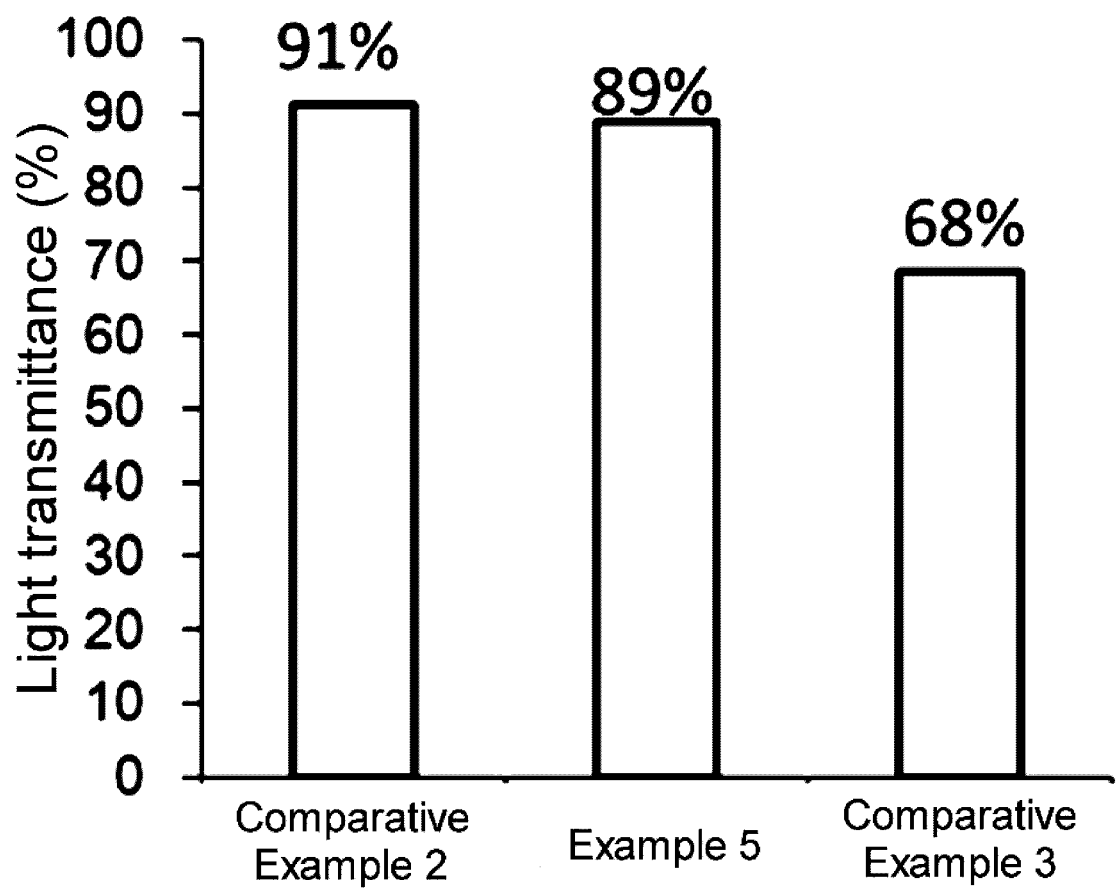

[FIG.5]
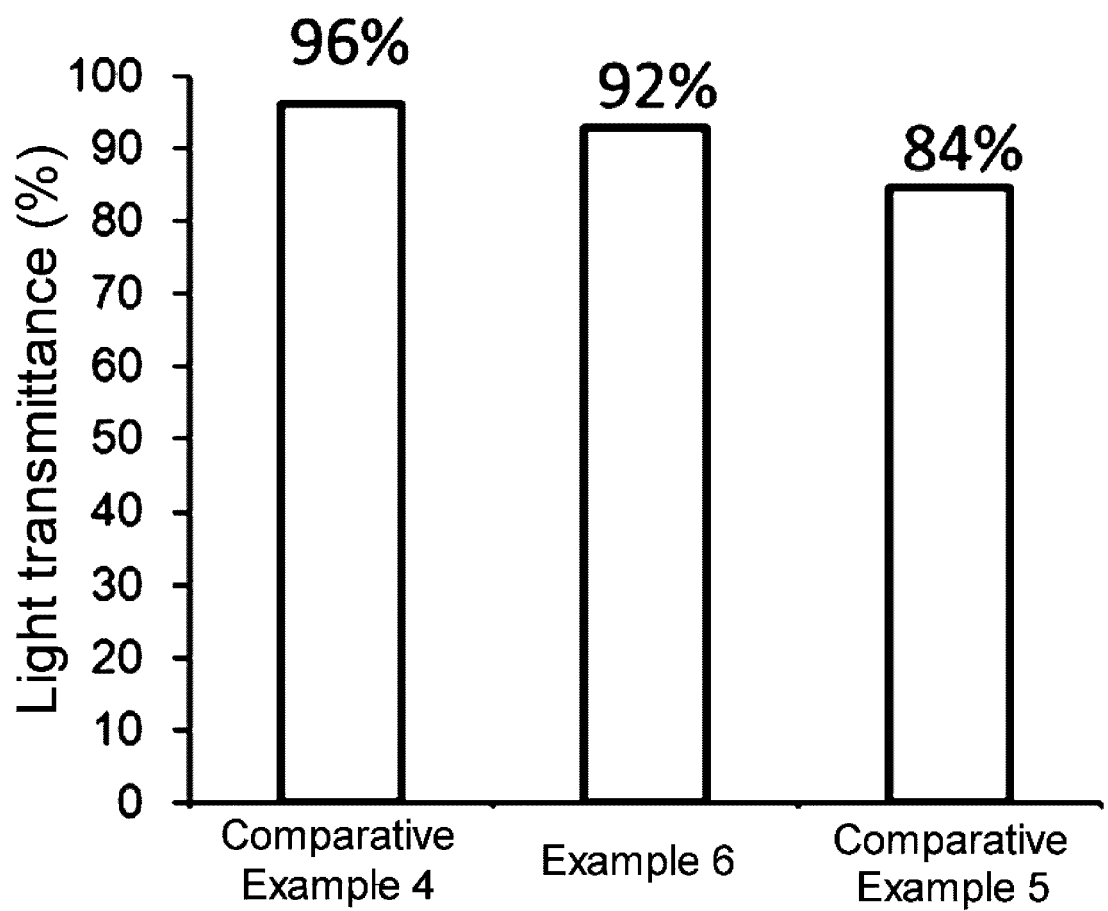

[FIG.6]
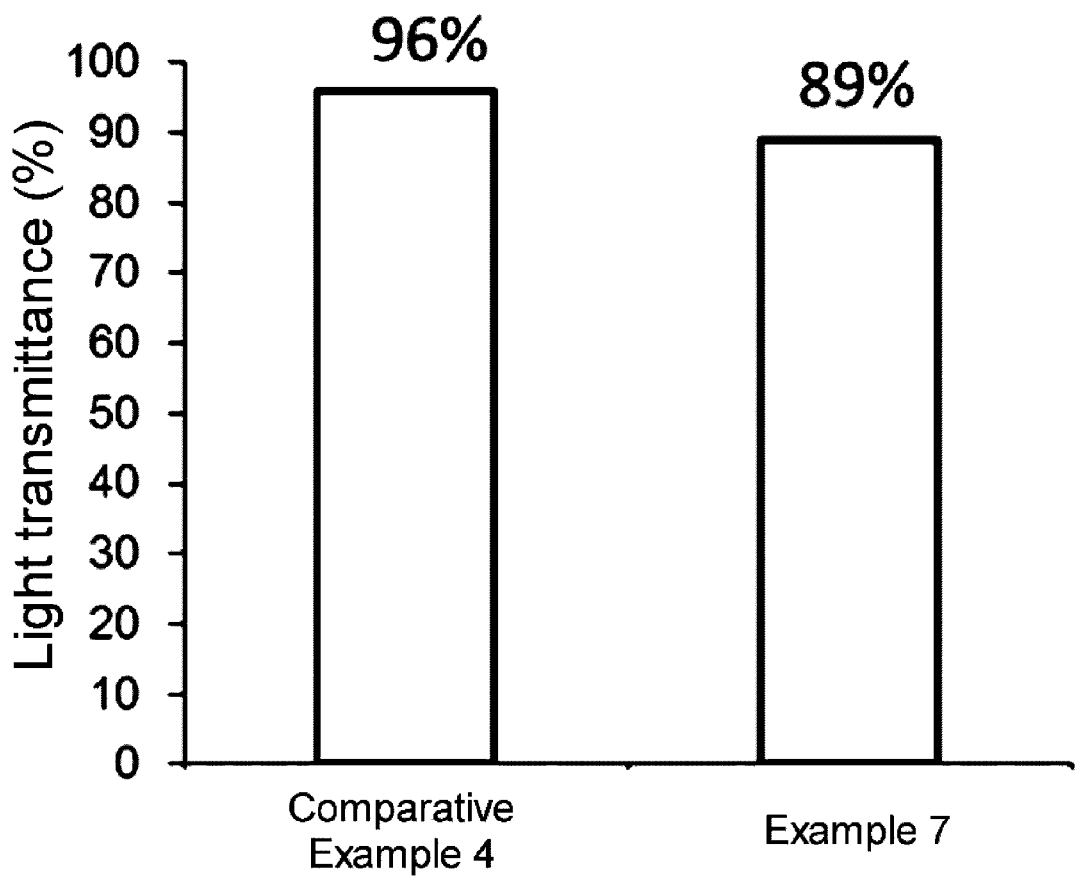

[FIG.7]
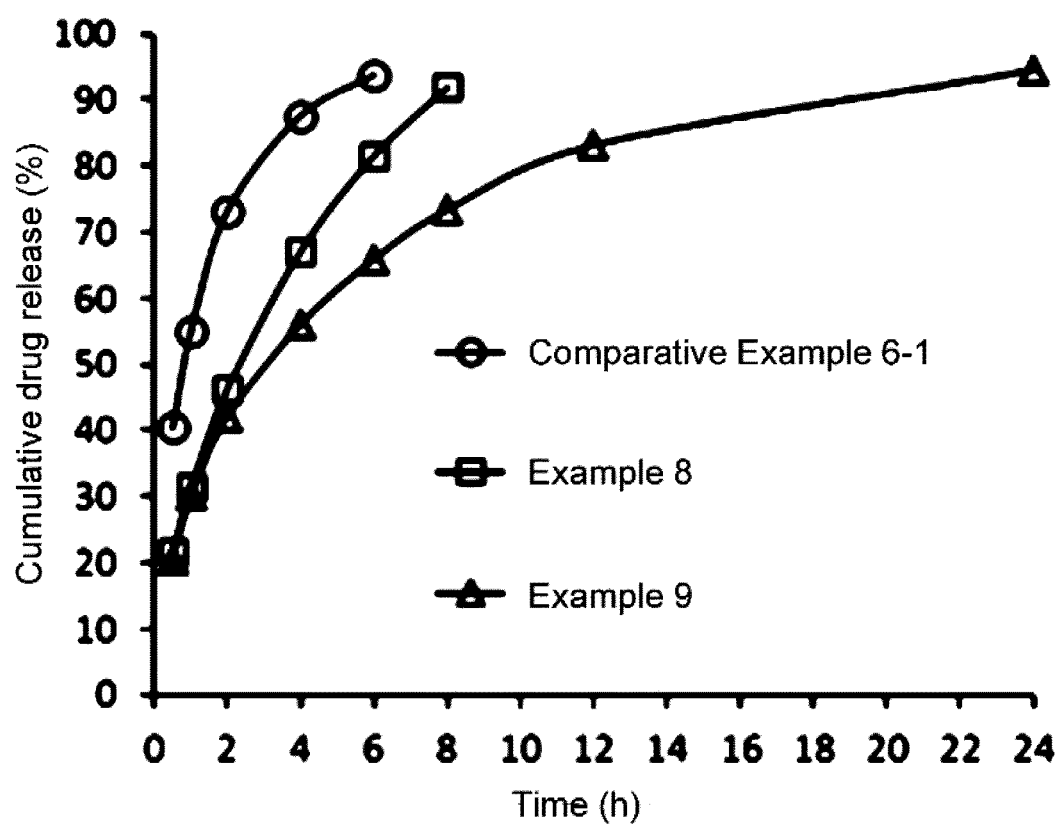

[FIG.8]
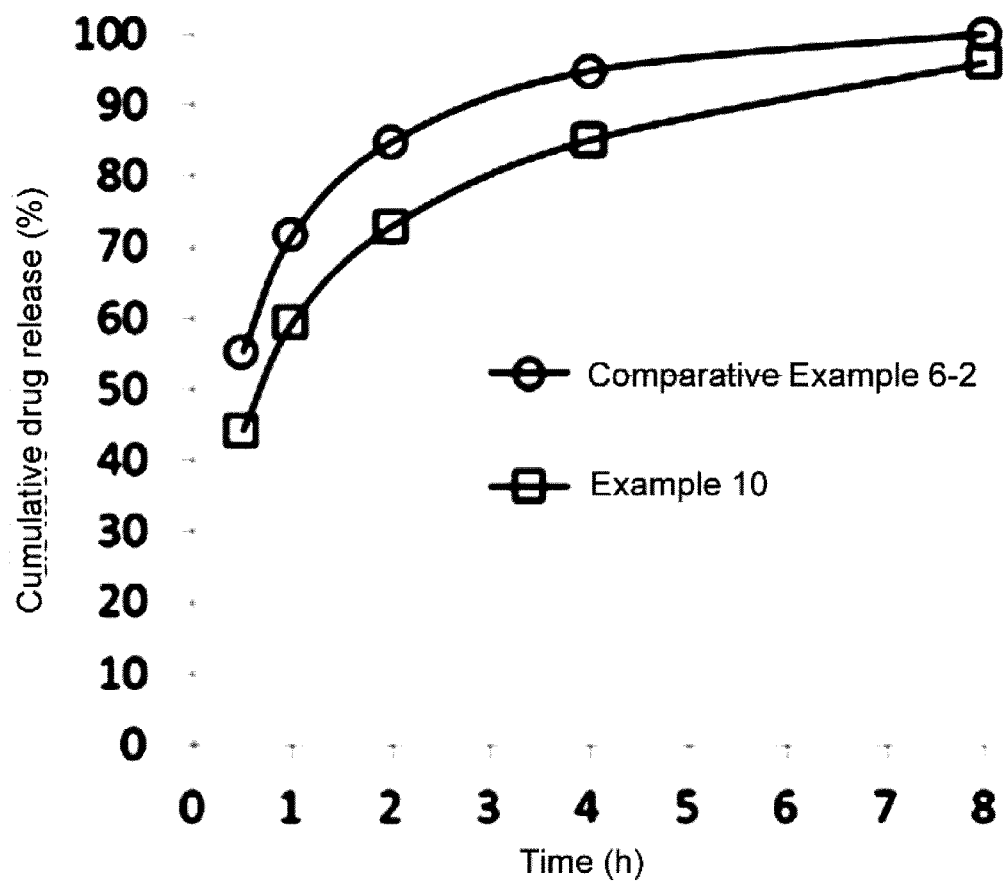

[FIG.9]
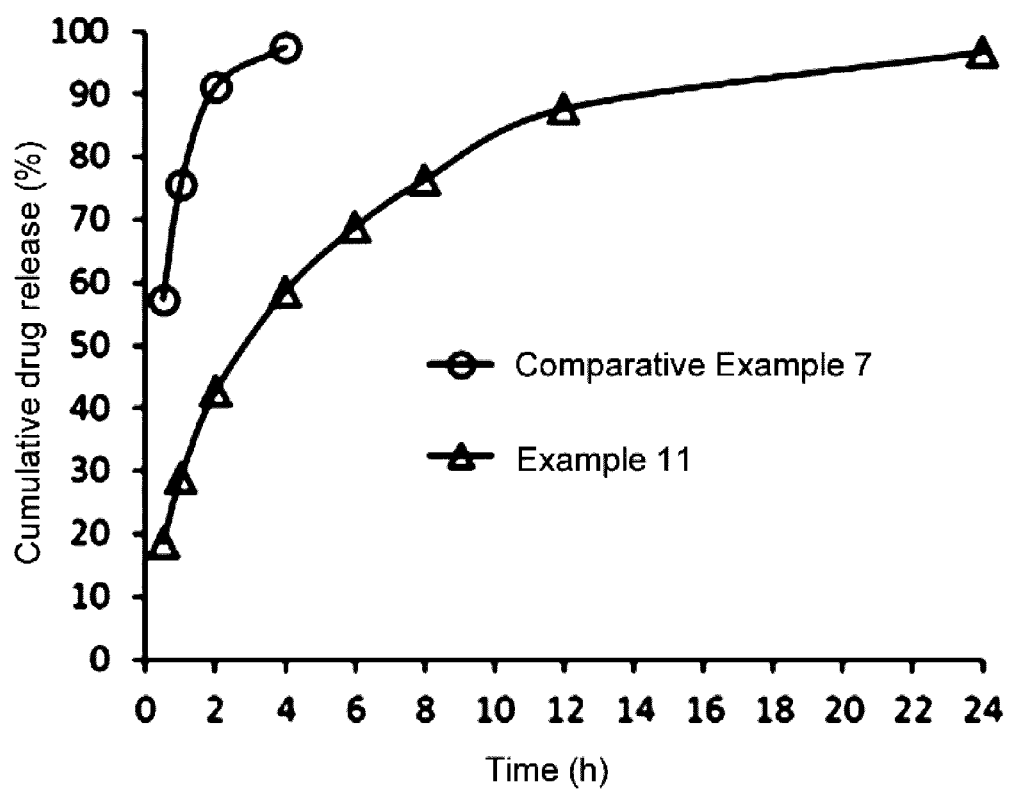

[FIG.10]
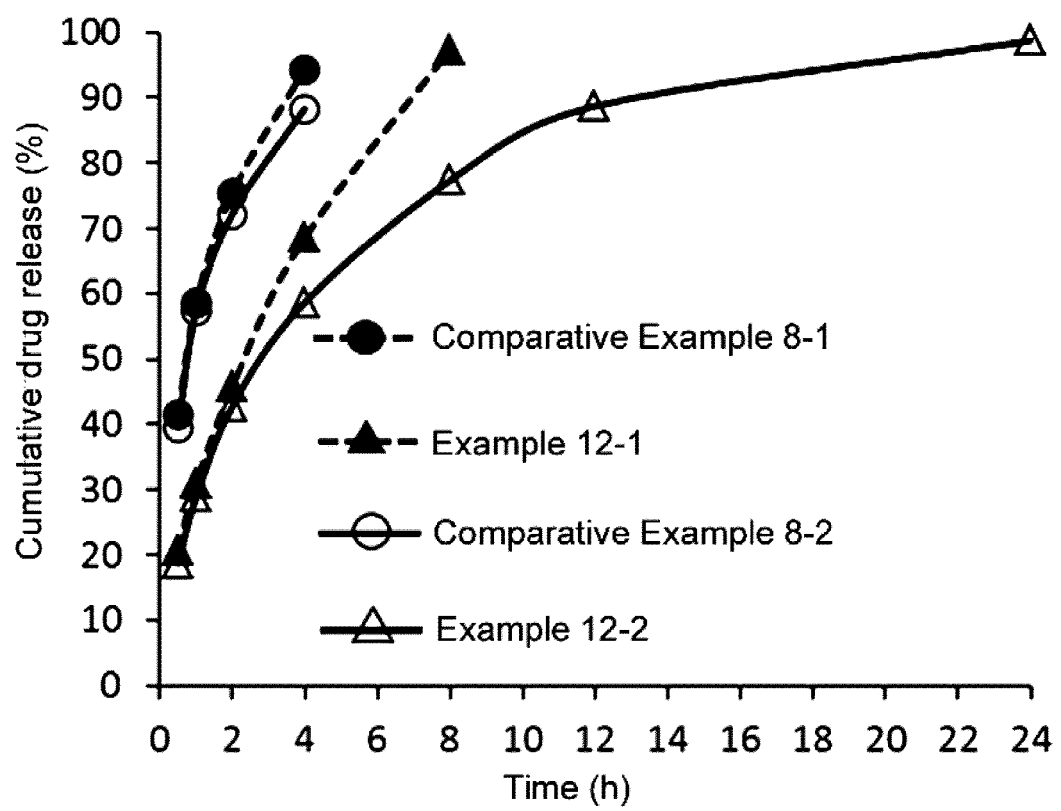

FUNCTIONAL POLYMER GEL CONTAINING ORGANIC NANOTUBES AND METHOD FOR PRODUCING SAME

CROSS REFERENCES TO RELATED APPLICATIONS

The present application claims the benefit of priority to Japanese Patent Application No. 2014-121914, filed on Jun. 12, 2014, the entire disclosure of which is incorporated herein by reference.

TECHNICAL FIELD

The present invention relates to functional polymer gels and methods for producing the same.

BACKGROUND ART

Organic nanotubes are tubular structures having hollow pores with an inner diameter of 7 to 200 nm that are formed by self-assembly of sugars, amino acids and other organic molecules. Various attempts have been made thus far to find their applications as nanocapsules (See, Non-Patent Document 1 below, which is incorporated herein by reference in its entirety). For example, organic nanotubes have been disclosed that are functionalized on their inner or outer surfaces in order to control the size, i.e., the outer and inner diameter, of the organic nanotubes (See, Non-Patent Document 2 and Patent Documents 1 and 2 below, each of which is incorporated herein by reference in its entirety). Further, organic nanotubes capable of encapsulating a protein in the small cavity within the tube or carrying biomaterials such as DNA or drugs on the outer surface of the tube and subsequently releasing them have been disclosed (See, Non-Patent Documents 3 to 5 below, each of which is incorporated herein by reference in its entirety).

Specifically, the present inventors have developed bicephalic lipids that have different hydrophilic moieties at both ends of a hydrophobic alkyl chain. The present inventors have reported the generation of asymmetric organic nanotubes with their inner and outer surfaces covered with different functional groups by self-assembly of such lipids (See, Non-Patent Documents 6 and 7 and Patent Document 1 below, each of which is incorporated herein by reference in its entirety). In some cases, this asymmetric characteristic has been utilized to achieve efficient encapsulation or sustained release of a biomaterial or a drug that has an opposite charge to that of the inner surface of the tube, by making use of the electrostatic attraction between the biomaterial or drug and the inner surface of the tube (See, Patent Document 3 and Non-Patent Document 6 below, each of which is incorporated herein by reference in its entirety). It has also been reported that the controlled drug release or protein refolding through encapsulation and release of a denatured protein can be achieved by introducing hydrophobic functional groups or the like selectively onto the inner surface of the tube (See, Patent Document 4, Non-Patent Documents 7 and 8 below, each of which is incorporated herein by reference in its entirety).

On the other hand, a drug delivery hydrogel has been reported that provides a varying sustained release rate of a protein or DNA from agarose gel depending on the guest size. The hydrogel is obtained by providing microtubes having an outer diameter in the order of about 0.5 micrometers and encapsulating a protein or DNA with a correspondingly large molecular weight, and subsequently dispersing the microtubes in an aqueous solution of agarose gel, followed by gelation of the solution (See, Non-Patent Documents 9 and 10, each of which is incorporated herein by reference in its entirety).

PRIOR ART DOCUMENTS

Patent Documents

[Patent Document 1] Japanese Patent Application Laid-Open Publication No. 2002-322190
[Patent Document 2] Japanese Patent Application Laid-Open Publication No. 2004-224717
[Patent Document 3] Japanese Patent Application Laid-Open Publication No. 2012-51828
[Patent Document 4] WO 2012/153576

Non-Patent Documents

[Non-Patent Document 1] Naohiro Kameta et al., Soft Matter, 7, (2001), 45339-4561.
[Non-Patent Document 2] Masaki Kogiso et al., Advanced Materials, 19(2007)242-246.
[Non-Patent Document 3] Hiroharu Yui et al., Chemistry Letters, 34(2005), 232-233.
[Non-Patent Document 4] Ipsita A. Banerjee et al., Bioconjugate Chemistry, 19, 2008, 2394-2400.
[Non-Patent Document 5] Xuehai Yan et al., Angewandte Chemie 46(2007)2431-2434.
[Non-Patent Document 6] Naohiro Kameta et al., Chemistry Materials, 16(2010)4217-4223.
[Non-Patent Document 7] Wuxiao Ding et al., Advanced Healthcare Materials, 1(2012)699-706.
[Non-Patent Document 8] Naohiro Kameta et al., ACS Nano, 6(2012)5249-5258.
[Non-Patent Document 9] Nancy J. Meilander et al., Journal of Controlled Release, 71(2001)141-152
[Non-Patent Document 10] Nancy J. Meilander et al., Journal of Controlled Release, 88(2003)321-331

DISCLOSURE OF THE INVENTION

Problems to be Solved by the Invention

With regard to the microtube-containing polymer gel disclosed in Non-Patent Documents 9 and 10, which is obtained by dispersing microtubes with an outer diameter of about 500 nm in an agarose gel, the microtubes can encapsulate only materials with large molecular weights, such as DNA and proteins. Furthermore, the inherent properties of the microtubes, such as interference of visible light and aggregation, tend to make the polymer gel turbid.

Thus, the present inventors considered that organic nanotubes with an inner diameter of 7 to 200 nm may be used instead of the above-described microtubes to encapsulate materials with relatively small molecular weights. Heretofore, however, organic nanotubes have been used in a liquid form, that is, a dispersion formed of organic nanotubes dispersed in a solvent, and no attempts have been made to use the organic nanotubes in a solid or semi-solid form.

In particular, organic nanotubes are formed by spontaneously assembling organic molecules in water, which provides them with their characteristic hydrophilic outer surfaces. As a result, organic nanotubes have extremely low dispersibility in the constituent monomers of a polymer gel and tend to associate together in the monomer to form aggregates. In an effort to reduce the interference of light, the present inventors have used fine organic nanotubes with an outer diameter of about 100 nm or less and have found that, as with the case of microtubes, organic nanotubes formed aggregates. When aggregation of organic nanotubes occurs in a polymer gel, the resulting polymer gel will have reduced transparency and decreased mechanical strength. As a result, the utility as a functional polymer gel will be decreased significantly.

On the other hand, the physical gel with embedded organic nanotubes as disclosed in Non-Patent Document 8 are obtained by increasing the concentration of organic nanotubes in water or a polar organic solvent so as to cause the organic nanotubes to form a network structure. However, the physical gel by its nature has low mechanical strength so that the network structure may readily disintegrate by external stimuli, such as stirring. As a result, the gel can disadvantageously revert to the flowable sol state.

Thus, functional polymer gels that are highly transparent, maintain their mechanical strengths, and contain uniformly dispersed organic nanotubes have yet to be achieved.

Accordingly, it is an objective of the present invention to provide a functional polymer gel that have high transparency and mechanical strength and are useful for making ophthalmic lenses, and in which organic nanotubes have been uniformly dispersed without forming aggregates during the complexation process of organic nanotubes in the polymer gel. It is also an objective of the present invention to provide a method for producing such functional polymer gels.

Means of Solving the Problems

In view of the above-described problems, the present inventors have conducted extensive studies and found that a transparent slurry-like organic nanotube dispersion can be stably obtained by dispersing organic nanotubes in a hydrophilic monomer that have high affinity for the organic nanotubes, and subsequently shaking the resultant dispersion for a predetermined period of time until it forms a slurry. The resulting slurry-like organic nanotube dispersion was then mixed with other copolymerizable monomers and a polymerization initiator to forma mixture in which the organic nanotubes were uniformly dispersed without forming aggregates. The mixture was then subjected to a copolymerization reaction to successfully form a highly transparent polymer gel containing uniformly dispersed organic nanotubes (Production Method A). Even surprisingly, by using hydrophilic monomers and copolymerizable monomers intended for use in the substrate of contact lenses, contact lenses containing dispersed organic nanotubes were made.

The present inventors also found that when an aqueous solution of a hydrophilic polymer such as gelatin was used in place of the hydrophilic monomer, a slurry-like organic nanotube dispersion was obtained by shaking a mixture of the aqueous hydrophilic polymer solution and the organic nanotubes for a predetermined period of time until the mixture becomes a slurry. The resulting slurry-like organic nanotube dispersion was subjected to a crosslinking reaction by mixing with a crosslinking agent or cooling to successfully form a highly transparent polymer gel in which organic nanotubes are uniformly dispersed without forming aggregates (Production Method B).

Each of the polymer gels obtained by Production Methods A and B above had high mechanical strength. Even surprisingly, a drug-containing polymer gel in which a drug is encapsulated within organic nanotubes in the polymer gel was obtained by immersing the organic nanotube-dispersed polymer gel obtained by Production Methods A and B in an aqueous drug solution or by using organic nanotubes already encapsulating a drug. Such a drug-containing polymer gel turned out to be a functional polymer gel in which the drug-release rate under physiological conditions can be controlled by modifying the inner surface of the organic nanotubes. The present invention was completed based on these findings and successful examples.

According to the present invention, there is provided a functional polymer gel containing an organic nanotube and having a light transmittance of 80% or higher.

Preferably, the functional polymer gel of the present invention is such that the functionality is sustained drug release.

Preferably, the functional polymer gel of the present invention is such that the organic nanotube is an organic nanotube having an outer diameter of 50 nm or less.

Preferably, the functional polymer gel of the present invention is such that the organic nanotube is an asymmetric organic nanotube that has an inner surface covered with a first functional group and an outer surface covered with a second functional group that is different from the first functional group.

Preferably, the functional polymer gel of the present invention is such that the organic nanotube is from 0.1 to 30 mass % with respect to the total amount of the polymer gel.

Preferably, the functional polymer gel of the present invention is a functional polymer gel formed of a crosslinked body of gelatin.

Preferably, the functional polymer gel of the present invention is a functional polymer gel formed of agarose.

Preferably, the functional polymer gel of the present invention is a functional polymer gel formed of a copolymer of polymerizable monomers.

According to another aspect of the present invention, there is provided a functional ophthalmic lens formed of the functional polymer gel of the present invention.

According to another aspect of the present invention, there is provided a method for producing a functional polymer gel, comprising the following Steps (1) to (3):

Step (1) of mixing an organic nanotube with a hydrophilic monomer in which the organic nanotube can be dispersed until a slurry-like material is produced, so as to obtain a slurry-like organic nanotube dispersion;

Step (2) of mixing the slurry-like organic nanotube dispersion with a monomer mixture containing a polymerizable monomer that is different from the hydrophilic monomer and a polymerization initiator to form a pre-polymerization solution; and Step (3) of subjecting the pre-polymerization solution to a copolymerization reaction to obtain a functional polymer gel.

According to another aspect of the present invention, there is provided a method for producing a functional polymer gel, comprising the following Steps (1)' and (2)':

Step (1)' of mixing an aqueous solution of a hydrophilic polymer capable of forming a polymer gel by crosslinking with an organic nanotube until a slurry-like material is produced, so as to obtain a slurry-like organic nanotube dispersion; and Step (2)' of subjecting the slurry-like organic nanotube dispersion to a crosslinking reaction to obtain a functional polymer gel.

Preferably, in the method for producing a functional polymer gel of the present invention, the mixing until a slurry is formed in Step (1) or Step (1)' is achieved by shaking at 15 to 40° C. for 1 to 24 hours.

Preferably, in the method for producing a functional polymer gel of the present invention, the slurry-like organic nanotube dispersion is a slurry-like organic nanotube dispersion in which the content of the organic nanotube is 60 mass % or less with respect to the hydrophilic monomer.

Preferably, in the method for producing a functional polymer gel of the present invention, the organic nanotube is an organic nanotube encapsulating a drug.

Preferably, the method for producing a functional polymer gel of the present invention further includes the step of immersing the functional polymer gel in an aqueous drug solution to obtain a functional polymer gel having a functionality of sustained drug release.

Preferably, in the method for producing a functional polymer gel of the present invention, the organic nanotube is an organic nanotube in which a hydrophobic functional group is introduced onto a part of the inner surface.

Advantageous Effects of Invention

The functional polymer gel of the present invention and the functional polymer gel obtained by the production methods of the present invention is a functional polymer gel that has organic nanotubes uniformly dispersed within the gel and has transparency and mechanical strength. The functional polymer gel is expected to have an application in ophthalmic lenses, in particular, sustained drug-release ophthalmic lenses in which the rate at which the drug encapsulated within the organic nanotubes is released can be controlled.

Also, since the organic nanotubes can encapsulate a drug or a useful biopolymer within their pores, the functional polymer gel of the present invention can be useful as a carrier for drugs or other materials in the fields of fine chemical industries, pharmaceutical or cosmetic products and is expected to find an application as a carrier for drug delivery systems.

Moreover, the use of asymmetric organic nanotubes having different inner and outer surface structures can improve the heat stability of the functional polymer gel of the present invention and can provide improved control over the sustained release of encapsulated drugs.

BRIEF DESCRIPTION OF DRAWINGS

FIG. 1 is a scanning transmission electron micrograph of an anionized organic nanotube described in Reference Example 1.

FIG. 2 is an optical micrograph of an anionized organic microtube described in Reference Example 1.

FIG. 3 is a diagram showing the results of evaluation of Examples 3 and 4 according to the evaluation method of sustained drug release.

FIG. 4 is a diagram showing the results of comparison of Examples 5 and Comparative Examples 2 and 3 according to the evaluation method of Transparency 2. Gelatin: Gelatin gel (Comp. Ex. 2), ONT-encapsulating gelatin: Organic nanotube-dispersed polymer gel (1) (Ex. 2), Microtube-encapsulating gelatin: Organic microtube-dispersed gelatin gel (Comp. Ex. 3).

FIG. 5 is a diagram showing the results of comparison of Examples 6 and Comparative Examples 4 and 5 according to the evaluation method of Transparency 2. Agarose: Agarose gel (Comp. Ex. 4), ONT-encapsulating agarose: Organic nanotube-dispersed polymer gel (2) (Ex. 3), Microtube-encapsulating agarose: Organic microtube-dispersed agarose gel (Comp. Ex. 5).

FIG. 6 is a diagram showing the results of comparison of Examples 7 and Comparative Examples 4 and 5 according to the evaluation method of Transparency 2. Agarose: Agarose gel (Comp. Ex. 4), Bicomponent organic nanotube-dispersed polymer gel (3) (Ex. 7), Microtube-encapsulating agarose: Organic microtube-dispersed agarose gel (Comp. Ex. 5).

FIG. 7 is a diagram showing the results of comparison of Examples 8 and 9 and Comparative Example 6-1 according to the evaluation method of sustained drug release.

FIG. 8 is a diagram showing the results of comparison of Example 10 and Comparative Example 6-2 according to the evaluation method of sustained drug release.

FIG. 9 is a diagram showing the results of comparison of Example 11 and Comparative Example 7 according to the evaluation method of sustained drug release.

FIG. 10 is a diagram showing the results of comparison of Example 12 and Comparative Example 8 according to the evaluation method of sustained drug release.

MODE FOR CARRYING OUT THE INVENTION

The present invention will now be described in details. All documents related to the present description are herein incorporated by reference in their entirety.

[1. Functional Polymer Gel of the Present Invention]

The functional polymer gel of the present invention is characterized by containing organic nanotubes and having a light transmittance of 80% or higher. The functional polymer gel of the present invention is a functional polymer gel to which particular functionalities derived from organic nanotubes contained in the gel have been imparted. The functionalities imparted by organic nanotubes are not particularly limited and include, for example, the ability to release a drug encapsulated within the organic nanotubes in a sustained manner.

As described in Examples below, the light transmittance of a functional polymer gel is defined as the light transmittance obtained by removing the functional polymer gel from water, wiping off excess moisture, and then measuring the light transmittance in a wavelength range of 280 to 380 nm using Hitachi U-3900H. The light transmittance of the functional polymer gel as measured by the above-described method is 80% or higher, preferably 85% or higher, more preferably 90% or higher, even more preferably 95% or higher, and still more preferably 98% or higher.

The organic nanotubes are not particularly limited and may be any tubular structure formed by self-assembly of amphipathic molecules such as sugars, amino acids, lipids and combinations thereof. Examples include a hollow fibrous membrane structure formed when a bimolecular membrane or a monomolecular membrane formed by self-assembly of amphipathic molecules in water is layered to form a cylindrical structure.

The inner diameter, the outer diameter, and the length of the organic nanotubes are not particularly limited; the organic nanotubes may have any inner diameter, outer diameter and length commonly known for nanotubes. For example, the organic nanotubes may have an inner diameter of about 6 to 100 nm, an outer diameter of about 10 to 150 nm, and a length of several μm to several hundred μm.

The outer diameter of organic nanotubes as used herein refers to an average outer diameter of organic nanotubes determined by measuring the outer diameter of about 30 organic nanotubes obtained from scanning transmission electron microscopy (STEM) or transmission electron microscopy (TEM) and averaging the results. When sufficient contrast cannot be obtained for fine organic nanotubes, measurements may be taken after staining the organic nanotubes with phosphotungstic acid, uranyl acetate or other suitable stains. The length and the inner diameter of organic nanotubes may be measured in a similar manner.

In view of the dispersibility when mixed with a hydrophilic monomer or a hydrophilic polymer or the transparency of the resulting slurry-like organic nanotube dispersion or functional polymer gel, the organic nanotubes preferably have a fine outer diameter. More preferably, the organic nanotubes have an extremely fine outer diameter, even more preferably, the organic nanotubes have an outer diameter of 50 nm or less, and still more preferably 20 nm or less when used in ophthalmic lenses.

When the organic nanotubes are used as a carrier for encapsulating a drug within the cavity thereof, the inner diameter of the organic nanotubes is preferably extremely fine according to the molecule size of the drug. The inner diameter of the organic nanotubes is more preferably 40 nm or less and even more preferably 20 nm or less in order to improve the retention rate of the drug. In this regard, the ratio of the outer diameter to the inner diameter (outer diameter:inner diameter) is for example in a range of 100:30 to 100:80 and preferably in a range of 100:45 to 100:60.

The length of the organic nanotubes is preferably from about 10 μm to 100 nm and more preferably 5 μm or less in view of the ease of handling during the production process. The length of the organic nanotubes may affect the viscosity of the slurry-like organic nanotube dispersion and the pre-polymerization solution prior to gelation. Specifically, when long organic nanotubes are used, the viscosity of the slurry-like organic nanotube dispersion and the pre-polymerization solution can be increased even at a low concentration of the organic nanotubes, making the production of the gel difficult. On the other hand, when short organic nanotubes are used, the increase in the viscosity of the slurry-like organic nanotube dispersion or the pre-polymerization solution tends to be suppressed even at a high concentration of the organic nanotubes, thus facilitating the production of the gel. Since the dispersibility in the solution also becomes relatively high for the short organic nanotubes, the resulting functional polymer gel can achieve transparency, which is advantageous when the functional polymer gel is used in ophthalmic lenses. The organic nanotubes may be shortened by using for example sonication (See, Wuxiao Ding et al., Journal of Controlled Release, 156 (2011) 70-75).

The gel-liquid crystal phase transition temperature of the organic nanotubes is not particularly limited. For example, the gel-liquid crystal phase transition temperature of the organic nanotubes depends on the type of the organic nanotubes used and may be any temperature that enables the functional polymer gel to endure the production process or the conditions under which it is used. Since the functional polymer gels are often subjected to heat sterilization when they are used in ophthalmic lenses, the gel-liquid crystal phase transition temperature of the organic nanotubes is preferably a temperature that allows such heat sterilization. More preferably, it is 100° C. or above to allow sterilization by boiling.

The structure of the organic nanotubes is not particularly limited since a functional polymer gel can be obtained whether the inner and outer surfaces of the organic nanotubes are the same or different from each other. However, the organic nanotubes are desirably asymmetric organic nanotubes that have inner and outer surfaces covered with different functional groups so as to provide, for example, the effective drug encapsulation into the functional polymer gel, the retention of drugs within the capsules, and the control over the drug release rate. Specifically, one preferred aspect of the structure of the organic nanotube is an asymmetric organic nanotube that has an inner surface covered with a first functional group and an outer surface covered with a second functional group that is different from the first functional group.

The outer surface of the organic nanotube preferably includes a hydrophilic functional group so that the dispersibility of the organic nanotubes in the resulting functional polymer gel can be maintained. Such a hydrophilic functional group may consist of one or more hydrophilic functional groups.

Examples of the hydrophilic functional groups to cover the outer surface of the organic nanotube include sugar residues such as glucose and glucosamine, hydroxyl group, polyethylene glycol groups having a molecular weight of up to about 5,000, carboxyl group, phosphate group, sulfonate group, primary to tertiary amino groups, and dipolar betaine groups. In order for the functional polymer gel of the present invention to be used in ophthalmic lenses, the outer surface of the organic nanotube is preferably covered with sugar residues or carboxyl groups, the above-described polyethylene glycol groups, and the aforementioned amino groups.

For the inner surface of the organic nanotube, ionic functional groups such as anionic or cationic functional groups, nonionic functional groups, amphiphilic functional groups having both hydrophilicity and hydrophobicity, and hydrophobic functional groups may be used. In particular, functional groups exhibiting electrostatic attraction or hydrophobic interaction with drugs are preferred in order to provide effective drug encapsulation into the organic nanotubes. The functional groups to cover the inner surface of the organic nanotube may consist of one or more functional groups. Specifically, the composition of the functional groups on the inner surface of the organic nanotube may desirably include two or more different kinds of functional groups at any ratio in order to provide the control over the drug release rate from the functional polymer gel. The drug release rate can be controlled by controlling this ratio.

Examples of the anionic functional group include carboxyl group, phosphate group, and sulfonate group. Examples of the cationic functional group include primary to tertiary amino groups. Examples of the nonionic functional group include hydroxyl group and oxyethylene groups having a chain length of up to 20 carbon atoms. Examples of the dipolar functional groups include betaines. Examples of the hydrophobic functional group include ester groups, acetyl groups, propanoyl groups, benzyloxycarbonyl groups, fluorenylcarbonyl groups, tert-butoxycarbonyl groups, and benzyl groups formed by methyl, ethyl, propyl, butyl, cyclopentyl, cyclopropyl, and benzyl.

In terms of efficient drug encapsulation into the organic nanotube, when the drug used has a positive or a negative charge, it is preferred to use an asymmetric organic nanotube with the inner surface covered with an oppositely charged ionic functional group. For nonionic, highly hydrophobic drugs, asymmetric organic nanotubes with the inner surface covered with hydrophobic functional groups are desirably used.

For example, drug-encapsulating functional polymer gels can be obtained by a method in which organic nanotubes already encapsulating a drug are used to form a gel, or by a method in which a formed functional polymer gel is immersed in a drug solution to encapsulate the drug into the organic nanotubes. Specifically, drug-encapsulating functional polymer gel can be obtained by the methods described in Patent Documents 3 and 4 and Non-Patent Document 7.

For a functional polymer gel using the asymmetric organic nanotube, the drug release rate can be set by introducing any ratio of a plurality of functional groups onto the inner surface of the organic nanotube, and adjusting the interaction between the inner surface of the organic nanotube and the drug. Since many drugs have an ionic functional group and a hydrophobic moiety, the drug release rate can be controlled by introducing an oppositely charged ionic functional group and a hydrophobic functional group onto the inner surface of the organic nanotube and varying their ratio. For drugs containing only hydrophobic functional groups, the drug release rate can also be controlled by varying the ratio of the hydrophobic groups to the hydrophilic groups on the inner surface of the organic nanotube.

The organic nanotubes can be made by any known method and are not particularly limited. The organic nanotubes for use in the present invention include, but not limited to, for example, an organic nanotube described in JP 2002-080489A, which is obtained by dissolving an O-glycoside-type glycolipid in water to saturation at a raised temperature, allowing the solution to slowly cool, and then allowing the solution to stand still at room temperature to cause self-molecular assembly and pseudo-crystallization; an organic nanotube described in JP 2002-322190A, which is obtained by dispersing an asymmetric bicephalic lipid having a D-glucopyranosyl group or a D-galactopyranosyl group in water at pH 2 to 8, dissolving the lipid by heating at 80 to 100° C., and subsequently allowing the solution to slowly cool; a low-molecular-weight organic compound-intercalated hollow fibrous organic nanotube described in JP 2008-264897A; an amide compound having a photoisomerizing group and an organic nanotube resulting from self-assembly of the compound described in JP 2011-046669A; an organic nanotube obtained by self-assembly of an boronic acid-glycolipid ester in an organic solution described in JP 2011-184365A; an organic nanotube described in JP 2008-030185A and JP 2004-224717A, which is obtained by dissolving a specific N-glycoside-type glycolipid or peptide lipid, an amphipathic molecule, in an organic solvent, and subsequently allowing the solution to slowly cool to cause self-assembly; an organic nanotube described in JP 2003-231100A, JP 2003-245900A, JP 2003-252893A, and JP 2003-259893A, which is obtained by self-assembly of a specific D-glycoside-type glycolipid that is an amphipathic molecule, or a mixture containing the glycolipid as the major component; and an organic nanotube obtained by self-assembly of glycylglycine, described in JP 2008-031152A and JP 2008-030185A.

The organic nanotube may contain a drug or a useful biomaterial within their cavities. The drug or the useful biomaterial is not particularly limited and may be produced by any known method. Examples include an organic nanotube complexed with nucleic acid, described in JP 2011-184391A; and a drug-encapsulating organic nanotube described in JP 2012-051828A; and a drug-encapsulating organic nanotube described in WO2012/153576 A1.

[2. Production Method A of the Present Invention]

Production Method A, which forms a first aspect of the present invention includes at least the following Steps (1) to (3):

Step (1) of mixing an organic nanotube with a hydrophilic monomer in which the organic nanotube can be dispersed until a slurry is formed, so as to obtain a slurry-like organic nanotube dispersion;

Step (2) of mixing the slurry-like organic nanotube dispersion with a monomer mixture containing a polymerizable monomer that is different from the hydrophilic monomer and a polymerization initiator to form a pre-polymerization solution; and Step (3) of subjecting the pre-polymerization solution to a copolymerization reaction to obtain a functional polymer gel.

In brief, Production Method A is a method in which in Step (1), an organic nanotube is mixed with a hydrophilic monomer having high affinity for the organic nanotube to form a slurry-like organic nanotube dispersion in which the organic nanotube is uniformly dispersed; then in Step (2), the slurry-like organic nanotube dispersion is mixed with a polymerizable monomer and other materials to form a pre-polymerization solution; and then in Step (3), the pre-polymerization solution is subjected to a copolymerization reaction to incorporate the organic nanotube, thereby obtaining a functional polymer gel throughout which the organic nanotube is uniformly dispersed. The functional polymer gel obtained by Production Method A is a polymer gel having transparency and strength and can thus be used in ophthalmic lenses.

In Production Method A, Steps (1) to (3) are not necessarily carried out sequentially; rather, various optional steps or processes may be added between steps or during each step as long as the objectives of the present invention can be achieved.

In Step (1) of Production Method A, an organic nanotube is combined with a hydrophilic monomer having high affinity for the organic nanotube and the mixture is stirred for mixing. Subsequently, the mixture is continuously shaken for a predetermined period of time until thoroughly mixed to obtain a slurry-like organic nanotube dispersion. By preparing the slurry-like organic nanotube dispersion in Step (1), the transparency can be imparted to the final functional polymer gel obtained by subsequent steps, making the polymer gel suitable for use in ophthalmic lenses.

The hydrophilic monomer that serves as a dispersion medium for the organic nanotube in Step (1) is not particularly limited and may be any monomer that contains a (meth)acrylic group or a vinyl group and at least one hydrophilic functional group in its molecule. Examples include hydroxymethyl(meth)acrylate, 2-hydroxyethyl (meth)acrylate, 2-hydroxypropyl(meth)acrylate, 2,3-dihydroxypropyl(meth)acrylate, 2-polyethylene glycol(meth) acrylate, acrylamide, 2-polypropylene glycol(meth)acrylate, N,N-dimethylmethacrylamide, N-vinylpyrrolidone (NVP), N,N-dimethylacrylamide (DMAA), (meth)acrylic acid, polyethylene glycol mono(meth)acrylate, glyceryl(meth) acrylate (glycerol(meth)acrylate), N-vinyl-N-methylacetamide, N-vinyl-N-ethylacetamide, N-vinyl-N-ethylformamide, and N-vinylformamide. These monomers may be used individually or two or more monomers may be mixed. As used herein, the term "(meth)acrylate" refers to either or both of acrylate and methacrylate. Of the hydrophilic monomers listed above, those with higher hydrophilicity are preferred in view of the affinity for the organic nanotube, especially for the organic nanotubes with the outer surface covered with a hydrophilic functional group. Specifically, glyceryl(meth)acrylate, hydroxyethyl(meth)acrylate, N,N-dimethylmethacrylamide, N-vinylpyrrolidone and (meth) acrylic acid are more preferred, and glyceryl acrylate and glyceryl methacrylate are even more preferred.

In Step (1), the amounts of the organic nanotube and the hydrophilic monomer to be added are not particularly limited and may be appropriately determined to provide ease of handling for the dispersion and the optical properties of the final polymer gel. For example, the content of the organic nanotube is from 0.01 to 60 mass %, preferably from 0.05 to 50 mass %, more preferably from 0.1 to 40 mass %, still more preferably from 0.1 to 30 mass %, and even more preferably from 1 to 20 mass % with respect to the hydrophilic monomer. If the content of the organic nanotube is greater than 60 mass %, then the final functional polymer gel tends to become turbid, which is unfavorable.

In Step (1), other components may be added during the mixing of the organic nanotube and the hydrophilic monomer as long as the dispersibility of the organic nanotube in the hydrophilic monomer or the transparency of the resulting slurry-like organic nanotube dispersion is not affected.

The mixing of the organic nanotube and the hydrophilic monomer in Step (1) may be carried out by any method that results in the organic nanotube substantially uniformly dispersed in the hydrophilic monomer and is not particularly limited. For example, the organic nanotube is weighed into the hydrophilic monomer and the mixture is stirred on a vortex mixer. Subsequently, the shaking or inverting is continued at 15 to 40° C., preferably at room temperature, for at least 1 hour or more, preferably for 1 to 24 hours, and more preferably for 1 to 12 hours to prepare a slurry-like organic nanotube dispersion. If the shaking is performed, it is preferably carried out at 250 to 5,000 rpm. The slurry-like organic nanotube dispersion may be any dispersion that forms a viscous mass, and is not particularly limited.

In Step (2) of Production Method A, the slurry-like organic nanotube dispersion obtained in Step (1) is mixed with a mixture containing at least a polymerizable monomer that is different from the hydrophilic monomer used in Step (1) and a polymerization initiator to obtain a copolymerizable pre-polymerization solution.

The polymerizable monomer is not particularly limited and may be any monomer commonly used in lens materials. Examples include hydrophilic monomers, such as hydroxymethyl(meth)acrylate, 2-hydroxyethyl(meth)acrylate, 2-hydroxypropyl(meth)acrylate, 2,3-dihydroxypropyl(meth)acrylate, 2-polyethylene glycol(meth)acrylate, acrylamide, 2-polypropylene glycol(meth)acrylate, N,N-dimethylmethacrylamide, N-vinylpyrrolidone (NVP), N,N-dimethylacrylamide (DMAA), (meth)acrylic acid, polyethylene glycol mono(meth)acrylate, glycerol(meth)acrylate, N-vinyl-N-methylacetamide, N-vinyl-N-ethylacetamide, N-vinyl-N-ethylformamide, and N-vinylformamide; and hydrophobic monomers, such as trifluoroethyl(meth)acrylate, methacrylamide, siloxanyl(meth)acrylate, methyl(meth)acrylate, n-butyl(meth)acrylate, tert-butyl(meth)acrylate, benzyl(meth)acrylate, ethylhexyl(meth)acrylate, and lauryl(meth)acrylate. These polymerizable monomers may be used individually or two or more monomers may be mixed. The amount of the polymerizable monomer is not particularly limited and may be any amount that results in the formation of a polymer gel by Step (3) described below. For example, the amount of the polymerizable monomer is from 10 to 90 mass %, preferably from 30 to 80 mass %, and more preferably from 50 to 70 mass % with respect to the total amount of the monomers that compose the polymer gel. If the amount of the polymerizable monomer is less than 10 mass %, then the polymer gel tends to become less formable and may be of less use in contact lenses.

The polymerization initiator is not particularly limited and may be any polymerization initiator used in the polymerization reaction of monomers. For example, thermal polymerization initiators and photopolymerization initiators, including peroxides and azo compounds, may be used with photopolymerization initiators being preferred. Examples of the photopolymerization initiator include IRGACURE 184, which is an alkylphenone compound, IRGACURE 819, which is an acylphosphine oxide compound, and IRGACURE 784, which is a titanocene compound. These polymerization initiators may be used individually or two or more initiators may be mixed. Though not particularly limited, the amount of the polymerization initiator is, for example, from 0.01 to 1.0 mass %, and preferably from 0.01 to 0.5 mass % with respect to the total amount of the monomers that compose the polymer gel. If the amount of the polymerization initiator is less than 0.01 mass %, then the polymerization reaction may be incomplete and polymerization gels with appropriate strength may not be obtained. If the amount of the polymerization initiator is 1.0 mass % or more, then the polymerization rate may be too fast and the reaction may become non-uniform. As a result, polymerization gels with appropriate strength may not be obtained.

In Step (2), other components may be added to the monomer mixture containing the polymerization monomer and the polymerization initiator. Typical examples of other components include crosslinkable monomers. The crosslinkable monomer is not particularly limited and may be any crosslinkable monomer used to form intermolecular crosslinks in a polymer gel to improve the shape stability and the strength of the gel. Examples include (meth)acrylate-based crosslinkable monomers, such as ethylene glycol di(meth)acrylate, diethylene glycol di(meth)acrylate, triethylene glycol di(meth)acrylate, propylene glycol di(meth)acrylate, dipropylene glycol di(meth)acrylate, tromethylolpropane tri(meth)acrylate, pentaerythritol tri(meth)acrylate, pentaerythritol tetra(meth)acrylate, and dipentaerythritol hexa(meth)acrylate; and vinyl-based crosslinkable monomers, such as allyl methacrylate, diallyl maleate, diallyl fumarate, diallyl succinate, diallyl phthalate, triallyl cyanurate, triallyl isocyanurate, diethylene glycol bisallyl carbonate, triallyl phosphate, triallyl trimellitate, diallyl ether, N, N-diallylmelamine, and divinylbenzene. Of these, bifunctional crosslinkable monomers are more preferred. Though not particularly limited, the amount of the crosslinkable monomer preferably is, for example, 5 mass % or less, and more preferably 3 mass % or less with respect to the total amount of the monomers that compose the polymer gel. If the amount of the crosslinkable monomer is greater than 5 mass %, then the crosslinking effect tends to be too strong and the resulting polymer gel may have decreased flexibility, making the polymer gel less useful in the application to contact lenses.

The preparation method of the monomer mixture is not particularly limited. For example, the monomer mixture may be prepared by weighing the polymerization monomer and the polymerization initiator according to the desired physical properties and mixing together using a vortex mixer.

In Step (3) of Production Method (A), the copolymerization reaction can be achieved under suitable conditions for the polymerization initiator and the monomer components. When a photopolymerization initiator is used as the polymerization initiator, for example, the pre-polymerization solution may be left to stand at 20 to 40° C. while irradiated with light until the copolymerization reaction is complete. The embodiment of Step (3) is not particularly limited. For example, the pre-polymerization solution may be placed in a mold of an ophthalmic lens and subjected to the copolymerization reaction to obtain a functional polymer shaped as the ophthalmic lens.

Once the slurry-like organic nanotube dispersion is obtained in Step (1), it is immediately mixed with the monomer mixture to obtain a pre-polymerization solution in which the aggregation is suppressed and the dispersibility is improved.

The content (i.e., proportion) of the organic nanotube in the pre-polymerization solution is, for example, from 0.1 to 10 mass %, more preferably from 0.1 to 5 mass % with respect to the total amount of the monomers that compose the polymer. By setting the content within these ranges, a functional polymer gel having the transparency suitable for ophthalmic lenses can be obtained.

In an alternative embodiment of Step (3), the pre-polymerization solution may be placed and subjected to the copolymerization reaction in a tubular container and subsequently cut or ground into the lens shape. Various other known methods may also be used.

In Step (4) of Production Method A, the functional polymer is hydrated and allowed to swell to obtain a hydrated functional polymer gel. The embodiment of Step (4) is not particularly limited. For example, the functional polymer obtained as the reaction product of Step (3), after released from the ophthalmic lens mold, is hydrated and allowed to swell to obtain a functional polymer gel.

The means to release the functional polymer from the mold is not particularly limited. For example, saline or a mixture of organic solvent/water may be used to cause the functional polymer to swell and release from the mold. The organic solvent used to cause the functional polymer to swell and release from the mold is not particularly limited and may be any organic solvent that can solvate the hydrophilic monomer or the polymerizable monomers and is miscible with water. Examples include primary and secondary alcohols. Specific examples of the organic solvent used to cause the functional polymer to swell and release from the mold include, but are not limited to, methanol, ethanol, propanol, isopropanol, n-butanol, and isobutanol. The organic solvents used to cause the functional polymer to swell and release from the mold may be used individually or two or more organic solvents may be mixed. Once released from the ophthalmic lens mold, a functional polymer separated from unreacted materials and having the organic nanotube dispersed therein can be obtained. The functional polymer obtained in this manner can then be hydrated and allowed to swell to cause the organic nanotubes to disperse in the polymer. As a result, a functional polymer gel having functionalities can be obtained. The liquids used to cause the functional polymer to swell and release from the mold include, but are not limited to, water, saline, and isotonic buffer.

[3. Production Method B of the Present Invention]

Production Method B, which forms a second aspect of the present invention includes at least the following Steps (1)' and (2)':

Step (1)' of mixing an aqueous solution of a hydrophilic polymer capable of forming a polymer gel by crosslinking with an organic nanotube until a slurry is formed, so as to obtain a slurry-like organic nanotube dispersion; and Step (2)' of subjecting the slurry-like organic nanotube dispersion to a crosslinking reaction to obtain a functional polymer gel.

In brief, Production Method B is a method in which in Step (1)', an organic nanotube is mixed with a hydrophilic polymer to form a slurry-like organic nanotube dispersion in which the organic nanotube is uniformly dispersed; and then in Step (2)', the slurry-like organic nanotube dispersion is subjected to a crosslinking reaction either by adding a crosslinking agent, or by placing the organic nanotube dispersion under conditions to cause a crosslinking reaction, to obtain a functional polymer gel in which the organic nanotube is uniformly dispersed. The functional polymer gel obtained by Production Method B is a polymer gel having transparency and strength and can thus be used in ophthalmic lenses.

In Production Method B, the crosslinking agent may be added during the mixing of the organic nanotube with the hydrophilic polymer in Step (1)'. When necessary, the method may include, after Step (2)', a step of immersing the functional polymer gel in aqueous solvent to remove the unreacted crosslinking agent.

In the Production Method B, the hydrophilic polymer may spontaneously gelate via physical or chemical crosslinking without using any crosslinking agent depending on the type of the hydrophilic polymer.

In Step (1)' of Production Method B, an aqueous solution of a hydrophilic polymer capable of forming a polymer gel by crosslinking is combined with an organic nanotube and the mixture is stirred for mixing. Subsequently, the mixture is continuously shaken for a predetermined period of time until thoroughly mixed to obtain a slurry-like organic nanotube dispersion. The polymer gel obtained by Production Method B includes a chemical gel formed of a covalently crosslinked structure resulting from the chemical reaction with the crosslinking agent, and a physical gel formed of a crosslinked structure resulting from the non-covalent association, such as hydrogen bonds, ionic bonds and hydrophobic interactions. The hydrophilic polymer of Step (1)' can form a polymer gel as the chemical gel or the physical gel. Examples of the hydrophilic polymer that can form a chemical gel include gelatin, ethyl cellulose, hydroxyethyl cellulose, hydroxypropyl cellulose, methyl cellulose, carboxymethyl cellulose, hyaluronic acid, polyethylene glycol, polyethylene oxide, and polyvinyl alcohol. Examples of the hydrophilic polymer that can form a physical gel include gelatin, agarose, agaropectin, amylose, amylopectin, carrageenan, carboxymethyl cellulose, methoxyl pectins, sodium alginate, guar gum, glucomannan, gellan gum, sodium polyacrylate, methoxyl pectin, and hyaluronic acid. The respective hydrophilic polymers may be used individually or two or more hydrophilic polymers may be mixed. Gelatin and agarose gel are preferably used as the hydrophilic polymer.

The mixing proportion of the organic nanotube with respect to the hydrophilic polymer is not particularly limited and may be determined to provide ease of handling for the dispersion and the optical properties of the resulting polymer gel. For example, the proportion of the organic nanotube is 40 mass % or less, preferably 30 mass % or less, and more preferably 25 mass % or less with respect to the aqueous solution of the water-soluble polymer to serve as the dispersion medium. If the mixing proportion of the organic nanotube is greater than 40 mass %, then the final functional polymer gel tends to become turbid, which is unfavorable.

In Step (1)', other components may be added during the mixing of the organic nanotube and the hydrophilic polymer as long as the dispersibility of the organic nanotube in the hydrophilic polymer or the transparency of the resulting slurry-like organic nanotube dispersion is not impaired.

The slurry-like organic nanotube dispersion can be obtained by weighing the organic nanotube into the hydrophilic polymer and mixing the mixture using a vortex mixer.

In Step (2)' of Production Method B, the slurry-like organic nanotube dispersion obtained in Step (1)' is subjected to a crosslinking reaction to obtain a functional polymer gel. A crosslinking agent may be added during the crosslinking reaction. For example, the crosslinking agent may be added to the slurry-like organic nanotube dispersion and the mixture is stirred to obtain a pre-gelation solution, which is then placed in an ophthalmic lens mold and subjected to a crosslinking reaction to obtain a functional polymer gel in which the hydrated organic nanotube is dispersed.

The crosslinking agent is not particularly limited and may be any crosslinking agent used to form intermolecular crosslinks in a polymer gel to improve the shape stability and the strength of the gel. Examples include polyfunctional crosslinking agents that can react with the amino group or the hydroxyl group in the hydrophilic polymer to form a crosslinked structure, such as formaldehyde, glutaraldehyde, polyfunctional epoxy crosslinking agents, polyfunctional isocyanate crosslinking agents, acyl azide compounds, carbodiimide, ethylene glycol diglycidyl ether, diglycerol triglycidyl ether, and divinylsulfonic acid. In order to form the crosslinked structure of a hydrophilic polymer that contains an amine in its molecule, such as gelatin, the crosslinking agent is preferably formaldehyde or glutaraldehyde.

For example, the amount of the crosslinking agent is preferably 5 vol % or less, and more preferably 3 vol % or less with respect to the total amount of the monomers that compose the polymer gel. If the amount of the crosslinking agent is greater than 5 vol %, then the crosslinked structure can be dense and the resulting polymer gel tends to have decreased flexibility. As a result, the polymer gel may be of less use especially when it is used in ophthalmic lenses.

In Step (2)', the functional polymer gel obtained as an organic nanotube-dispersed crosslinked body is preferably immersed in an aqueous solution to remove the unreacted crosslinking agent. Examples of the aqueous solution include water, saline, and isotonic buffer.

Similar to Production Method A, Production Method B may employ, in addition to subjecting to a crosslinking reaction in an ophthalmic lens mold, any known method such as crosslinking in a tubular container, followed by machining into a desired shape. The means to release the functional polymer gel from the mold is not particularly limited and may include the method described in Production Method A. For example, saline or a mixture of organic solvent/water may be used to cause the functional polymer to swell at a varying degree and release from the mold.

One specific aspect of the functional polymer gel obtained in Production Methods A and B is a sustained drug release polymer gel that contains a drug encapsulated within the organic nanotube. The production methods of the sustained drug release polymer gel are generally divided into pre-loading methods and post-loading methods.

A pre-loading method uses an organic nanotube that has a drug encapsulated therein, whereas a post-loading method involves immersing an organic nanotube-containing polymer gel in an aqueous drug solution in order to encapsulate the drug within the organic nanotube.

The organic nanotubes to serve as a drug carrier are classified into two types: symmetric organic nanotubes that have the same structure on their inner and outer surfaces, and asymmetric organic nanotubes that have different structures on their inner and outer surfaces. The type of the organic nanotubes may be appropriately selected depending on their intended purposes.

The drug release rate from the drug-encapsulating organic nanotube can be controlled by taking advantage of the interaction between the inner surface structure of the organic nanotube and the chemical structure of the drug. In particular, when an asymmetric organic nanotube is selected as the drug carrier, different functional groups can be introduced onto the inner surface of the organic nanotube at any desired ratio, which, in conjunction with the structure of the encapsulated drug, allows more effective control over the sustained release.

For example, when a drug containing both an ionic functional group and a hydrophobic moiety in one molecule is selected, the sustained release can be controlled by introducing an ionic functional group having an opposite charge to the ionic functional group of the drug and a hydrophobic moiety onto the inner surface of the organic nanotube at any ratio. In comparison, when a drug containing only a hydrophobic moiety is selected, the sustained release can be controlled by varying the ratio of the hydrophobic functional groups introduced into the organic nanotube as desired.

Specific combinations of an anionic group and a hydrophobic functional group include, for example, a combination of carboxyl group and benzyloxycarbonyl group, and a combination of carboxyl group and methyl ester. Specific combinations of a cationic group and a hydrophobic functional group include, for example, a combination of amino group and benzyloxycarbonyl group or acetyl group.

The present invention will now be described in further detail with reference to the following Examples, which are not intended to limit the present invention. The present invention may take various forms to the extent that the objectives of the present invention are achieved.

EXAMPLES

Reference Example 1

Production Method of Organic Microtube and Microtube

According to Non-Patent Document 7 and Patent Document 4, the following three types of organic nanotube were obtained: a hydrophobized organic nanotube formed by self-assembly of the lipid (I) represented by the general formula (I) below; an anionized organic nanotube formed by self-assembly of the lipid (II) represented by the general formula (II) below; and a partially hydrophobized organic nanotube formed by self-assembly of a mixture of the lipid (II) represented by the general formula (II) below and the lipid (III) represented by the general formula (III) below (lipid (II):lipid (III)=3:1 molar ratio). Also, according to the article by Kameta et al., a cationized nanotube formed by self-assembly of the lipid (IV) represented by the general formula (IV) below was obtained (Naohiro Kameta et al., Chemistry Materials, 21 (2009) 5892-5898). These four types of organic nanotube each had an inner tube diameter of about 7 nm, an outer diameter of 15 nm, and a length of about 2 to 5 μm. FIG. 1 shows a scanning transmission electron micrograph and a schematic diagram of the anionized organic nanotube formed from the lipid (II) represented by the general formula (II), along with a photographic image of a container holding an aqueous dispersion obtained by dispersing the anionized organic nanotube in water.

Further, according to Non-Patent Document 9, an organic microtube was formed using a commercially available phospholipid (1,2-bis(10,12-tricosadiynoyl)-sn-glycero-3-phosphocholine, Avanti Polar Lipid, Inc., USA). The organic microtube had an outer diameter of about 500 nm and a length of about 50 μm. FIG. 2 shows an optical micrograph and a schematic diagram of the resulting organic microtube, along with a photographic image of a container holding an aqueous dispersion obtained by dispersing the organic microtube in water.

(Chemical formula 1)

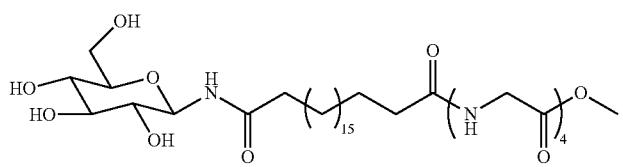
(I)

(Chemical formula 2)

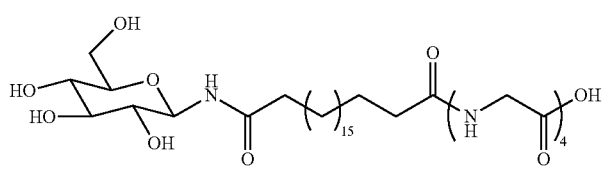
(II)

(Chemical formula 3)

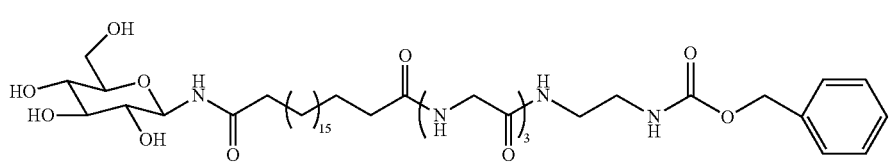
(III)

(Chemical formula 4)

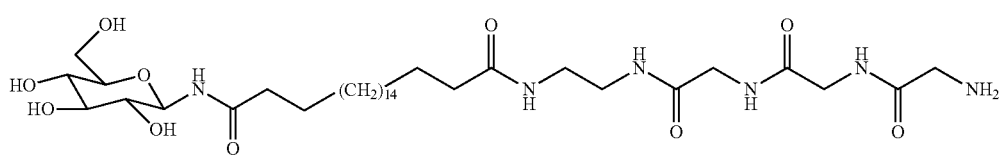
(IV)

Reference Example 2

Production Method of Drug-Encapsulating Organic Nanotube

A. Encapsulation of Methylene Blue into Anionized Organic Nanotube

An MB-encapsulating anionized organic nanotube encapsulating methylene blue was obtained by mixing an aqueous dispersion of the anionized organic nanotube obtained in Reference Example 1 (pH=about 7.0, 1 mL, 10 mg/mL) with an aqueous solution of methylene blue (MB) (73 μL, 10 mg/mL). From the feed ratio (MB:ONT=1:7 molar ratio), the encapsulation efficiency of MB into the anionized organic nanotube was determined to be close to 100%.

In contrast, methylene blue (MB) was not encapsulated into the organic microtube formed in Reference Example 1 even when a large excess of MB (10,000 molar equivalents relative to the lipid molecule present in the microtube) was added to the organic microtube.

B. Encapsulation of Methylene Blue into Partially Hydrophobized Organic Nanotube Similarly, an MB-encapsulating partially hydrophobized organic nanotube encapsulating methylene blue was obtained by mixing an aqueous dispersion of the partially hydrophobized organic nanotube obtained in Reference Example 1 (pH=about 7.0, 1 mL, 5 mg/mL) with an aqueous solution of methylene blue (MB) (36 μL, 10 mg/mL).

C. Encapsulation of Sodium Azobenzene-4,4'-Dicarboxylate (Azo) into Cationized Organic Nanotube Similarly, an Azo-encapsulating cationized organic nanotube encapsulating sodium azobenzene-4,4'-dicarboxylate was obtained by mixing an dispersion of the cationized organic nanotube obtained in Reference Example 1 (pH=about 7.5, 1 mL, 5 mg/mL) with an aqueous solution of sodium azobenzene-4,4'-dicarboxylate (Azo) (36 μL, 7 mg/mL). From the feed ratio (Azo:ONT=1:7 molar ratio), the encapsulation efficiency of Azo into the cationized organic nanotube was determined to be close to 100%.

Evaluation Methods

A. Transparency 1

The light transmittance was determined by removing the organic nanotube-dispersed polymer gel from water, wiping off excess moisture, and then measuring the light transmittance in a wavelength range of 280 to 380 nm using Hitachi U-3900H.

B. Transparency 2

The light transmittance was determined by removing the organic nanotube-dispersed polymer gel from water, wiping off excess moisture, and then measuring the light transmittance at a wavelength of 350 nm using Hitachi U-3900H.

C. Tensile Strength

According to JIS K 7113 "Tensile test method of plastics", test pieces were prepared and measured for strength.

A circle indicates that the tensile strength was 1.5 MPa or higher. A cross indicates that the tensile strength was less than 1.5 MPa.

D. Moisture Content

The organic nanotube-dispersed polymer gel was removed from water and excess moisture was wiped off. The mass ($W_1$) in the hydrated state was then measured. Subsequently, the polymer gel was dried in a dryer at 60° C. for 24 hours and the mass ($W_2$) was measured. The determined masses were used in the following equation to calculate the moisture content.

Moisture Content(mass %)=$[(W_1-W_2)/W_1]\times 100$

E. Sustained Drug Release

The sustained release of the encapsulated drug was determined by the following procedure.

The MB- or Azo-encapsulating organic nanotube-dispersed polymer gel was placed in a 10 mL PBS solution and the solution was gently shaken on a bioshaker. After 0.5, 1, 2, 4, 6, 8, 24, 48, 72, and 96 hours, 5 mL of the discharged solution was collected and 5 mL of a fresh PBS solution was supplemented. The concentration of MB in the collected discharged solution was determined by light (663 nm) and the cumulative discharged amount was calculated.

[Example 1] Production Method of Anionized Organic Nanotube-Dispersed Ophthalmic Lens 5 mass % of the hydrophobized organic nanotube (ONT) obtained in Reference Example 1 (externally added) was added to 50 mass % of glyceryl methacrylate (GLM) and the mixture was stirred on a vortex mixer for 30 min to disperse ONT into GLM. Subsequently, the mixture was shaken at room temperature for 8 hours (at 1500 rpm) to obtain a slurry-like organic nanotube dispersion.

Next, a monomer mixture was prepared by mixing together 50 mass % of 2-hydroxyethyl methacrylate (HEMA), 0.3 mass % of ethylene glycol dimethacrylate (EDMA) (externally added), and 0.3 mass % of IRGACURE 819 (polymerization initiator) (externally added). The above-described slurry-like organic nanotube dispersion was then weighed into this mixture and the mixture was further stirred to obtain a pre-polymerization solution. The concentrations of ONT, EDMA and IRGACURE 819 were based on the total amount of GLM and HEMA.

The pre-polymerization solution was then poured into a mold of an ophthalmic lens and was polymerized by irradiating with a fluorescent lamp at room temperature for 2 hours to obtain an organic nanotube-dispersed polymer.

Subsequently, the organic nanotube-dispersed polymer was removed from the mold and was immersed in pure water for 4 hours to allow to swell by hydration. This resulted in an anionized organic nanotube-dispersed ophthalmic lens. The resulting ophthalmic lens was composed of a colorless and transparent hydrated gel with a moisture content of 50%.

[Example 2] Production Method of Cationized Organic Nanotube-Dispersed Ophthalmic Lens A cationized organic nanotube-dispersed ophthalmic lens was obtained in the same manner as in Example 1, except that the cationized organic nanotube derived from the general formula (IV) was used.

[Example 3] Production Method of Anionized Organic Nanotube-Dispersed Ophthalmic Lens Having Methylene Blue Encapsulated by Post-Loading Method The anionized organic nanotube-dispersed ophthalmic lens prepared in Example 1 was immersed in an aqueous methylene blue solution (2 mg/mL, 20 mL) at room temperature for 2 hours, such that methylene blue was encapsulated by the action of electrostatic attraction toward the inner surface of the tube. This resulted in a drug-encapsulating organic nanotube-dispersed ophthalmic lens.

[Example 4] Production Method of Cationized Organic Nanotube-Dispersed Ophthalmic Lens Having Sodium Cromoglycate Encapsulated by Post-Loading Method The cationized organic nanotube-dispersed ophthalmic lens prepared in Example 2 was immersed in an aqueous solution of sodium cromoglycate (2 mg/mL, 20 mL) at room temperature for 2 hours, such that sodium cromoglycate was encapsulated by the action of electrostatic attraction toward the inner surface of the tube. This resulted in a drug-encapsulating organic nanotube-dispersed ophthalmic lens.

[Example 5] Production Method of Anionized Organic Nanotube-Dispersed Gelatin Gel by Complexation of Anionized Organic Nanotube with Gelatin An aqueous dispersion of the anionized organic nanotube obtained in Reference Example 1 (1 mL, Conc. 10 mg/ml) was mixed with an aqueous gelatin solution (Conc. 200 mg/mL, 1 mL) in a 2.5 mL plastic syringe to obtain a slurry-like pre-crosslinking solution.

To the pre-crosslinking solution, 40.0 µL of glutaraldehyde was added quickly and the syringe was repeatedly inverted to uniformly mix the mixture. The mixture was then allowed to stand still for 8 hours at room temperature to obtain an organic nanotube-dispersed crosslinked body. The resulting organic nanotube-dispersed crosslinked body was sliced together with the syringe to isolate a disk-shaped crosslinked body (10 (w/w) % gelatin) having a diameter of 0.9 cm and a thickness of 0.5 mm.

The disk-shaped crosslinked body was then immersed in a phosphate buffer (pH 7.0) to remove unreacted glutaraldehyde. This gave an organic nanotube-dispersed polymer gel (1). The resulting organic nanotube-dispersed polymer gel (1) was a slightly yellow and transparent hydrated gel.

[Example 6] Production Method of Anionized Organic Nanotube-Dispersed Agarose Gel by Complexation of Anionized Organic Nanotube with Agarose An aqueous solution of the anionized organic nanotube obtained in Reference Example 1 (5 mg/mL, 1 ml) was mixed with 1 mL of an aqueous agarose solution (20 mg/mL, 1 mL) in a 2.5 mL plastic syringe at 55° C. and the resulting solution was cooled to room temperature to obtain an organic nanotube-dispersed crosslinked body. The resulting organic nanotube-dispersed crosslinked body was sliced together with the syringe to isolate a disk-shaped composite gel (1% (w/w) agarose) having a diameter of 0.9 cm and a thickness of 0.5 mm. The composite gel was designated as organic nanotube-dispersed polymer gel (2).

[Example 7] Production Method of Bicomponent Organic Nanotube Composite Agarose Gel by Complexation of Two Organic Nanotubes with Agarose An aqueous solution of the anionized organic nanotube (5 mg/mL, 0.5 mL) and an aqueous solution of the cationized organic nanotube (5 mg/mL, 0.5 mL), both obtained in Reference Example, and 1 mL of an aqueous agarose solution (20 mg/mL, 1 mL) were mixed together in a 2.5 mL plastic syringe at 55° C. and the resulting solution was cooled to room temperature to obtain an organic nanotube-dispersed crosslinked body. The resulting organic nanotube-dispersed crosslinked body was sliced together with the syringe to isolate a disk-shaped composite gel (1% (w/w) agarose) having a diameter of 0.9 cm and a thickness of 0.5 mm. The composite gel was designated as organic nanotube-dispersed polymer gel (3).

[Examples 8 and 9] Production Method of MB-Encapsulating Organic Nanotube-Dispersed Gelatin Gel Having Methylene Blue Encapsulated by Pre-Loading Method A drug-encapsulating organic nanotube-dispersed polymer gel (1) was obtained in the same manner as in Example 1 except that an aqueous solution (1 mg/mL, conc. 10 mg/mL) that contains the MB-encapsulating anionized organic nanotube encapsulating methylene blue obtained in Reference Example 2A was used (Example 8). During the removal of unreacted glutaraldehyde, the discharge of MB from the drug-encapsulating organic nanotube-dispersed polymer gel was not observed.

Similarly, a drug-encapsulating organic nanotube-dispersed polymer gel (2) was obtained in the same manner as in Example 1, except that an aqueous solution (1 mL, conc. 5 mg/mL) of the MB-encapsulating partially hydrophobized organic nanotube encapsulating methylene blue obtained in Reference Example 2B was used (Example 9). During the removal of unreacted glutaraldehyde, the discharge of MB from the drug-encapsulating organic nanotube-dispersed polymer gel was not observed.

[Example 10] Production Method of Organic Nanotube-Dispersed Gelatin Gel Having Methylene Blue Encapsulated by Post-Loading Method The organic nanotube-dispersed polymer gel (1) prepared in Example 5 was treated in a phosphate buffer (pH 7.0) for 24 hours to disperse the organic nanotube. Subsequently, an aqueous MB solution (2 mg/mL) was added and the polymer gel was incubated for 2 hours to encapsulate MB by the action of electrostatic attraction toward the inner surface of the tube. This gave a drug-encapsulating organic nanotube-dispersed crosslinked body.

The drug-encapsulating organic nanotube-dispersed crosslinked body was washed with a copious amount of water to remove unencapsulated MB. This resulted in a drug-encapsulating organic nanotube-dispersed polymer gel (3).

[Example 11] Production Method of MB-Encapsulating Anionized Organic Nanotube-Dispersed Agarose Gel Having Methylene Blue Encapsulated by Pre-Loading Method A drug-encapsulating organic nanotube-dispersed polymer gel (4) was obtained in the same manner as in Example 6, except that an aqueous solution (1 mL, conc. 5 mg/mL) that contains the MB-encapsulating anionized inner surface organic nanotube encapsulating methylene blue obtained in Reference Example 2A was used.

[Example 12] Production Method of MB-Encapsulating Organic Nanotube/Azo-Encapsulating Organic Nanotube-Dispersed Agarose Gel Having Methylene Blue and Sodium Azobenzene-4,4'-dicarbxylate Encapsulated by Pre-Loading Method A bicomponent organic nanotube-dispersed polymer gel (6) was obtained in the same manner as in Example 9, except that the polymer gel was sequentially immersed in an aqueous solution (1 mL, conc. 5 mg/mL) of the MB-encapsulating partially hydrophobized organic nanotube obtained in Reference Example 2A and an aqueous solution (0.9 mL, conc. 5 mg/mL) of the Azo-encapsulating cationized organic nanotube similarly obtained in Reference Example 2C.

Comparative Example 1

5 mass % of ONT obtained in Reference Example 1 (externally added) was weighed into a monomer mixture composed of 50 mass % of GLM, 50 mass % of HEMA, 0.3 mass % of EDMA (externally added), and 0.3 mass % of IRGACURE 819 (2.4 µl) (externally added) and the mixture was stirred. Subsequently, the monomer mixture was poured into a mold of an ophthalmic lens and was polymerized by irradiating with a fluorescent lamp for 2 hours to obtain an organic nanotube-dispersed polymer. The concentrations of ONT, EDMA and IRGACURE 819 were based on the total amount of GLM and HEMA.

The resulting organic nanotube-dispersed polymer was removed from the mold and was immersed in pure water for 4 hours to allow to swell by hydration. This resulted in an ophthalmic lens. The resulting ophthalmic lens was a turbid hydrated gel with a moisture content of 50%.

Comparative Example 2

A gelatin gel was prepared in the same manner as in Example 2, except that 1 mL of an aqueous gelatin solution was used alone without the aqueous dispersion of the anionized organic nanotube. The excess glutaraldehyde was removed by immersing the gelatin gel in water.

Comparative Example 3

An organic microtube-dispersed gelatin gel was prepared in the same manner as in Example 2, except that the aqueous dispersion of the anionized organic microtube obtained in Reference Example 1 was not used.

Comparative Example 4

An agarose gel was prepared in the same manner as in Example 3, except that 1 mL of an aqueous agarose solution was used alone without the aqueous dispersion of the anionized organic nanotube obtained in Reference Example 1.

Comparative Example 5

An microtube-dispersed agarose gel was prepared in the same manner as in Example 3, except that the microtube obtained in Reference Example 1 was not used.

Comparative Example 6

The gelatin gel prepared in Comparative Example 2 was immersed in an aqueous MB solution (2 mg/mL) to obtain two pieces of MB-containing gelatin gel. These pieces were designated as Comparative Examples 6-1 and 6-2, respectively.

Comparative Example 7

The agarose gel prepared in Comparative Example 4 was immersed in an aqueous MB solution (2 mg/mL) to obtain MB-containing agarose gel.

Comparative Example 8

The agarose gel prepared in Comparative Example 4 was sequentially immersed in an aqueous MB solution (0.36 mg/mL, 100 µl) and an aqueous Azo solution (0.25 mg/mL, 900 µl) to obtain MB/Azo-containing agarose gel.

Comparison of Examples 1 and 2 and Comparative Example 1

Transparency 1, the moisture content and the strength were measured for Examples 1 and 2 and Comparative Example 1 according to the respective evaluation methods. The results are shown in Table 1. As shown in Table 1, Examples 1 and 2 exhibited significantly higher transparency than Comparative Example 1.

TABLE 1

| Item | Moisture Content (%) | Transparency (%) | Strength (MPa) |
| --- | --- | --- | --- |
| Example 1 | 38.5 | 98.3 | 1.93 |
| Example 2 | 40.4 | 98.9 | 1.57 |
| Comp. Ex. 1 | 38.1 | 52.8 | 1.67 |

Evaluation of Sustained Drug Release of Examples 3 and 4

The drug-encapsulating anionic organic nanotube-dispersed ophthalmic lens of Example 3 and the drug-encapsulating cationic organic nanotube-dispersed ophthalmic lens of Example 4 were evaluated according to the evaluation method of sustained drug release. The results are shown in FIG. 3. As shown in FIG. 3, the organic nanotube-dispersed ophthalmic lenses of Examples 3 and 4 each exhibited slow sustained release of the drug.

Comparison of Example 5 and Comparative Examples 2 and 3

Example 5 and Comparative Examples 2 and 3 were evaluated according to the evaluation methods of Transparency 2 and Transparency 3. The results for Transparency 2 and Transparency 3 are shown in FIG. 4 and FIG. 5, respectively. As shown in FIGS. 4 and 5, Example 5 exhibited higher transparency than Comparative Example 3.

Comparison of Example 6 and Comparative Examples 4 and 5

Example 6 and Comparative Examples 4 and 5 were evaluated according to the evaluation methods of Transparency 2 and Transparency 3. The results for Transparency 2 and Transparency 3 are shown in FIG. 6 and FIG. 7, respectively. As shown in FIGS. 6 and 7, Example 6 exhibited higher transparency than Comparative Example 5.

Comparison of Example 7 and Comparative Examples 4 and 5

Example 7 and Comparative Examples 4 and 5 were evaluated according to the evaluation method of Transparency 2. The results are shown in FIG. 8. As shown in FIG. 8, Example 7 exhibited higher transparency than Comparative Example 5.

Comparison of Examples 8 and 9 and Comparative Example 6-1

The two drug-encapsulating organic nanotube-dispersed polymer gels (1) and (2) of Examples 8 and 9, as well as the MB-containing gelatin gel prepared in Comparative Example 6-1, were evaluated according the evaluation method of sustained drug release. The results are shown in FIG. 9. As shown in FIG. 9, it is observed that the simple gel of Comparative Example 6-1 rapidly discharged MB, whereas the organic nanotube-dispersed hydrogels of Examples 8 and 9 (Pre-loading method) each exhibited controlled sustained release of MB.

The sustained release rate was particularly suppressed in the MB-encapsulating partially hydrophobized organic nanotube-dispersed gelatin gel of Example 9, which has a partially hydrophobized inner surface. This suggests that the sustained release rate of methylene blue from the organic nanotube-dispersed polymer gel can be controlled by controlling the number of hydrophobic moieties introduced onto the inner tube surface.

Comparison of Example 10 and Comparative Example 6-2

The drug-encapsulating organic nanotube-dispersed polymer gel (3) of Example 10 and the MB-containing gelatin gel of Comparative Example 6-2 were evaluated according the evaluation method of sustained drug release. The results are shown in FIG. 10. As shown in FIG. 10, it is observed that the simple gel of Comparative Example 6-2 rapidly discharged MB, whereas the sustained release of methylene blue from the organic nanotube-dispersed hydrogel of Example 10 (Post-loading method) can be controlled.

Comparison of Example 11 and Comparative Example 7

The drug-encapsulating organic nanotube-dispersed polymer gel (5) of Example 11 and the MB-containing agarose gel of Comparative Example 7 were evaluated according the evaluation method of sustained drug release. The results are shown in FIG. 11. As shown in FIG. 11, it is observed that the simple gel of Comparative Example 7 rapidly discharged MB, whereas the sustained release of methylene blue from the partially hydrophobized organic nanotube-dispersed hydrogel of Example 11 (Pre-loading method) is controlled.

Comparison of Example 12 and Comparative Example 8

The bicomponent drug-encapsulating organic nanotube-dispersed polymer gel (6) of Example 12 and the MB/Azo-containing agarose gel of Comparative Example 8 were evaluated according the evaluation method of sustained drug release. The results are shown in FIG. 12. As shown in FIG. 12, it is observed that the simple gel of Comparative Example 8 rapidly discharged MB and Azo, whereas the sustained release of methylene blue and sodium azobenzene-4,4'-dicarboxylate from the bicomponent organic nanotube-dispersed hydrogel of Example 12 (Pre-loading method) is controlled.

INDUSTRIAL APPLICABILITY

The polymer gels complexed with the organic nanotubes obtained by the above-described production methods can be used as a lens material. By providing the fine spaces attributable to the organic nanotubes within the polymer gel, the development of lens materials that have sustained drug release property and other functionalities can be made possible. In addition, the functional polymer gels of the present invention can be used in DDS applications as, for example, patches capable of sustained drug release.

The invention claimed is:

1. A method for producing a functional polymer gel, comprising:
    Step (1) of mixing an organic nanotube with a hydrophilic monomer in which the organic nanotube can be dispersed until a slurry-like material is produced, so as to obtain a slurry-like organic nanotube dispersion, wherein mixing is by shaking at 15 to 40° C. for 1 to 24 hours;
    Step (2) of mixing the slurry-like organic nanotube dispersion with a monomer mixture containing a polymerizable monomer that is different from the hydrophilic monomer and a polymerization initiator to form a pre-polymerization solution;
    Step (3) of subjecting the pre-polymerization solution to a copolymerization reaction to obtain a functional polymer; and
    Step (4) of hydrating and allowing to swell the functional polymer to obtain a functional polymer gel.

2. The method for producing a functional polymer gel of claim 1, wherein the slurry-like organic nanotube dispersion is a slurry-like organic nanotube dispersion in which the content of the organic nanotube is 60 mass % or less with respect to the hydrophilic monomer.

3. The method for producing a functional polymer gel of claim 1, wherein the organic nanotube is an organic nanotube encapsulating a drug.

4. The method for producing a functional polymer gel of claim 1 further including the step of immersing the functional polymer gel in an aqueous drug solution to obtain a functional polymer gel having a functionality of sustained drug release.

5. The method for producing a functional polymer gel of claim 1, wherein the organic nanotube is an organic nanotube in which a hydrophobic functional group is introduced onto a part of the inner surface.

* * * * *